(12) United States Patent
Fromovich et al.

(10) Patent No.: US 7,396,232 B2
(45) Date of Patent: * Jul. 8, 2008

(54) PERIOSTEAL DISTRACTION

(76) Inventors: Ophir Fromovich, Hahagana 17, Petach Tikva (IL); Benzion Karmon, Ben Zakkai 17, Elad 48900 (IL)

(*) Notice: Subject to any disclaimer, the term of this patent is extended or adjusted under 35 U.S.C. 154(b) by 415 days.

This patent is subject to a terminal disclaimer.

(21) Appl. No.: 10/861,401

(22) Filed: Jun. 7, 2004

(65) Prior Publication Data

US 2005/0059864 A1 Mar. 17, 2005

Related U.S. Application Data

(63) Continuation-in-part of application No. PCT/IL02/00987, filed on Dec. 5, 2002.

(51) Int. Cl.
*A61C 8/00* (2006.01)
(52) U.S. Cl. .................. 433/215; 433/173; 606/105
(58) Field of Classification Search .......... 433/215, 433/189, 172–174; 623/8, 17.17; 606/192, 606/198, 105, 90
See application file for complete search history.

(56) References Cited

U.S. PATENT DOCUMENTS

| | | | |
|---|---|---|---|
| 5,511,565 A * | 4/1996 | Syers .................. 128/898 |
| 5,695,338 A * | 12/1997 | Robert ................. 433/215 |
| 5,882,353 A * | 3/1999 | VanBeek et al. ............ 623/8 |
| 5,961,329 A * | 10/1999 | Stucki-McCormick ...... 433/173 |
| 5,976,142 A * | 11/1999 | Chin .................... 606/73 |
| 5,980,252 A * | 11/1999 | Samchukov et al. ....... 433/215 |
| 6,030,218 A * | 2/2000 | Robinson ............... 433/173 |
| 6,050,819 A * | 4/2000 | Robinson ............... 433/173 |
| 6,270,346 B1 * | 8/2001 | Grabenhofer et al. ...... 433/173 |
| 6,409,764 B1 * | 6/2002 | White et al. ............ 623/16.11 |
| 2001/0012607 A1 * | 8/2001 | Robinson ............... 433/215 |

* cited by examiner

*Primary Examiner*—Cary E O'Connor
(74) *Attorney, Agent, or Firm*—Mark M. Friedman

(57) ABSTRACT

Devices and methods for gradual displacing of the soft tissues covering bones. The gap developing between the bone and the displaced soft tissue will be filled with bone callus as it is in distraction osteogenesis. The devices and methods allow formation of bone in distraction osteogenesis without cutting a segment of the bone. The devices and methods are particularly useful in dental implantology for vertical ridge augmentation by displacing the periosteal tissue and for sinus lift by displacing the Schneiderian membrane. The devices and methods can also regenerate soft tissue between the bone and the displaced soft tissue.

73 Claims, 12 Drawing Sheets

PERIOSTEAL DISTRACTION

This application is a Continuation-in-Part of PCT/IL02/00987 filed Dec. 5, 2002, which claims priority U.S. patent application Ser. No. 10/002,135 filed Dec. 5, 2001.

FIELD AND BACKGROUND OF THE INVENTION

The present invention relates to improved methods and devices for tissue regeneration especially bone augmentation.

Treatment of edentulous patients with osseointegrated fixtures made of titanium is a well-known procedure in the art. The procedure includes installing a fixture in the alveolar bone of an at least partially edentulous jaw. Usually several months are required for proper healing after fixture installation.

After healing, an abutment is installed on the upper portion of the fixture. After several weeks, an artificial tooth may be mounted on the abutment and the procedure is complete.

Installation of implants requires sufficient alveolar bone, generally about 10 mm height and 6 mm width.

When a tooth is removed, the alveolar bone is gradually resorbed because of the absence of stimulus of ossification-inducing pressure from the teeth. As the resorption process advances, the size of the bone gets reduced, i.e. the bone on which the dental roots are positioned—the alveolar ridge start shrinking.

The absence of just one tooth can cause modifications throughout the dental arch and even prompt a possible softening (loss of insertion) which may cause the loss of other teeth. The absence of several teeth aggravates the problem. Bone loss may finally modify the patient's appearance and, depending on the loss, may make him incapable of receiving bridges, implants or even dentures.

It is then necessary to carry out several surgical operations to reconstruct the alveolar ridge of the maxilla or mandible.

Although these methods of surgical reconstruction have been successfully performed, this type of operation has had drawbacks. Certain methods have involved opening the periosteal tissue (which is the tissue surrounding the bone and is easily detached from the bone) along the entire length of the atrophic alveolar ridge and then placing a bone graft material and a membrane on top of the graft and then suturing the delicate periosteal tissue back together to cover the membrane. The role of the membrane is to maintain the bone graft in its place and to prevent the mucoepithelium from growing into the graft and interfering with the process of bone regeneration. This surgical operation called guided bone regeneration has had drawbacks resulting from the lack of enough soft tissue to cover the enlarged bone.

In order to overcome some of these drawbacks, another small surgical procedure is done before the performance of the procedures mentioned above. In this procedure an expandable device is placed beneath the periosteum through a small incision. This device made of silicon is gradually filled with a liquid through a cannula. While this expandable device expands tension is transferred to the periosteum leading to enlargement of the periosteum. When the periosteum reached the desired dimension the expandable device is taken out and a bone graft is placed as described above, but now there is no need to stretch the mucoperiosteal tissue therefore reducing the complications.

This procedure has two significant drawbacks:
1. Two surgical procedures are needed. A small procedure for insertion of the expandable device and a big procedure for placing the bone graft and the membrane.
2. All the hazards of a relative big operation in the mouth.

Another method to regenerate bone is distraction osteogenesis, which is a process whereby bone is stretched to increase bone volume. According to distraction osteogenesis processes, at least one portion of a bone is at least partially separated from the bone. The position of the portion is gradually altered with respect to the bone. Time is then provided for new bone to fill in the space between the portion and the overall bone.

When distraction osteogenesis is used in dentistry dental applications, a portion of a patient's jawbone will be at least partially severed from the overall jawbone. The jawbone segment may then be gradually separated from the rest of the jawbone. New bone then fills in the space between the segment and the jawbone. By increasing the volume of bone in the jawbone, additional area can be provided to anchor or at least more securely anchor dental implants. Distraction osteogenesis can also be used in dental applications simply to strengthen a location on the jawbone to increase the bone volume at that location even if implants are not to be secured in the jawbone at that location.

These techniques of distraction osteogenesis has some disadvantages:
1) It is difficult technically to the surgeon.
2) It is traumatic to the patient.
3) This procedure can be done if the height of the ridge is at least 6 mm
4) This technique is not using the new materials available today that enhance bone regeneration.

The present invention is unique because these methods and devices allow distraction osteogenesis without cutting a segment of the bone therefore the procedure is simple minimal invasive and not traumatic. In the present invention only the periosteal tissue is separated from the bone. In another embodiment of the invention materials that enhance bone regeneration can be added to the distraction gap.

SUMMARY OF THE INVENTION

The present invention provides methods and devices to regenerate tissues especially bone. The device is preferably made from a movable element preferably in the shape of a plate placed between the bone and the soft tissue preferably subperiostealy and a force inducing mechanism to allow gradual and preferably controlled displacement of the periosteal tissue or the soft tissue from the bone. The plate preferably is not connected to the tissue and this is different from the bone distractors. As the plate is displaced a space is created between the bone and plate. In the preferred embodiments the plate is moving perpendicular to the plane of the plate (if the plate is not flat the plane is the tangent plane to the center of the plate). The boundaries of the space are the bone and the displaced soft tissue. The unique space created by the present invention is bounded from one side by the bone and from all other sides by the soft tissue. Since there is nothing between the tissues and the space the space is filled with new regenerated tissue. If the conditions are enabling bone growth the new tissue will be bone. If the conditions are not appropriate for bone regeneration the soft tissue will regenerate and will fill the space. In some preferred embodiments the device can include elements to prevent the soft tissue from entering the space and to allow only to the bone tissue to regenerate. The device can be made fully or partially of a bioresorbable material.

The device is activated one or more times every few days till the desired displacement is reached. The activation can be done continuously over several hours. While the plate moves it conducts tensile forces to the surrounding tissue, which reacts in proliferation and enlargement. The gap between the plate and the bone is filled with bone callus if the periosteal tissue is displaced slowly. At the same time bone substitute materials can be added through a filling element. After the desired enlargement is reached the filling element can be pull out if necessary. The end result is a new or an enlarged compartment in the body filled with new bone callus and bone substitute materials.

The insertion of the device can be through a small incision to a subperiosteal tunnel so all the process is done with almost no surgery.

There are many possible implementations of the device and method depending on several factors:
1. The place the device is inserted into.
2. The filling material.
3. The shape of the plate.
4. The kind of filling element that is in use.
5. The kind of material the plate is made of.

The devices and methods are particularly useful for plastic surgery, orthopedic surgery and, dental implantology.

In dental implantology the configuration of the device has to take in consideration the opposite jaw. The device is especially useful for vertical ridge augmentation. When elevating the movable element, which is preferably in the shape of a plate, the most upper region of the device must be low enough in order to allow closure of the mouth without biting on the device. In the present invention all the embodiments will allow the most upper region of the force inducing mechanism above the gums (if it is above the gums) to be elevated less than the elevation of the movable element. In some preferred embodiments the most upper region of the force inducing mechanism above the gums (if it is above the gums) is elevated no more then 3 mm above the gums, while the plate is elevated much more, and in some preferred embodiments it is not elevated at all or it is completely beneath the gums. In the preferred embodiments of this invention the height between the most upper region of the force inducing mechanism at the end of the elevation and the movable element at the beginning of the elevation is less than the elevation of the movable element plus the height between the most upper region of the force inducing mechanism and the movable element at the end of the elevation. In other wards the basic principal of the present invention is a device for insertion between the bone and the adjacent tissue that includes a soft tissue displacer and a displacing mechanism to control the distance of the soft tissue displacer from the bone. The device is configured so after the final displacement the distance between the most upper region of the displacing mechanism and the soft tissue is less then distance between the soft tissue and the bone. (If the device is completely beneath the soft tissue then the distance between the most upper region of the displacing mechanism and the soft tissue is negative).

Other objects and features of the present invention will become apparent in the following detailed description when taken in connection with the accompanying drawings, which disclose one embodiment of the invention. It is to be understood that the drawings are designed for the purpose of illustration only and are not intended as a definition of the limits of the invention.

Thus, according to the teachings of the present invention there is provided a method for expanding, stretching, displacing or regenerating tissues comprising: inserting at the bone soft tissue interface at least part of a displacing device comprising a soft tissue displacer and a displacing mechanism configured to displace the soft tissue displacer from the bone so as to create a space between the bone and the soft tissue, the displacing mechanism is configured so the distance between the highest point of the displacing mechanism and the soft tissue is less than the distance between the soft tissue and the bone.

According to a further feature of the present invention the only limitation between the space and the soft tissue is the soft tissue displacer.

According to a further feature of the present invention the bone is the alveolar ridge and the bone is left open to the oral cavity.

According to a further feature of the present invention the soft tissue displacer is a movable element and the displacing mechanism is a force inducing mechanism configured after activation so as to move the movable element, the movable element is configured after activation of the force inducing mechanism so as to induce forces displacing at least part of the soft tissue, the method includes after insertion of the movable element between the soft tissue and the bone activating of the force inducing mechanism.

According to a further feature of the present invention the soft tissue is the periosteal tissue.

According to a further feature of the present invention the soft tissue is the Schneiderian membrane of the sinus.

Thus, according to the teachings of the present invention there is provided, a method for expanding, stretching or displacing bone tissue comprising: (a) inserting subperiostealy at least part of a displacing device comprising a movable subperiosteal element and a force inducing mechanism configured after activation so as to move the movable subperiosteal element; the movable subperiosteal element is configured after activation of the force inducing mechanism so as to induce forces displacing at least part of the periosteal tissue. (b) activating said force inducing mechanism.

According to a further feature of the present invention the activation is performed in a plurality of stages separated by at least a number of hours, each stage incrementally displacing the periosteal tissue.

According to a further feature of the present invention the device includes a mechanism to expand horizontally to reach horizontal diameter larger than the diameter of the hole the device was inserted through. This method is especially useful in the maxillary sinus.

According to a further feature of the present invention, the displacing is done continuously over a period of time.

According to a further feature of the present invention, the speed of the displacing of the periosteal tissue is appropriate for formation of bone callus between the bone tissue and the periosteal tissue.

According to a further feature of the present invention, the force inducing mechanism induces forces continuously.

According to a further feature of the present invention, the force inducing mechanism is a pump.

According to a further feature of the present invention, the force inducing mechanism is pressure beneath the movable subperiosteal element.

According to a further feature of the present invention, the activation is done by introducing a biocompatible filling material beneath the movable subperiosteal element.

According to a further feature of the present invention, the displacing is combined with introducing a biocompatible filling material beneath the movable subperiosteal element.

According to a further feature of the present invention, the biocompatible filling material includes material for promoting the growth of bone.

According to a further feature of the present invention, the biocompatible filling material includes material for promoting the growth of bone.

According to a further feature of the present invention, the displacing device includes a filling conduit partially inserted into the tissue.

According to a further feature of the present invention, the filling conduit includes a one-directional valve.

According to a further feature of the present invention, the filling conduit includes a sealing means for sealing the filling conduit.

According to a further feature of the present invention, the method further comprising introducing disinfecting material into the filling conduit.

According to a further feature of the present invention, the filling conduit includes at least one fixation component configured to allow fixation of the filling conduit to the tissue.

According to a further feature of the present invention, the displacing device is formed at least in part from a bio-dissipative material.

According to a further feature of the present invention, the displacing device is formed at least in part from a self-expanding material.

According to a further feature of the present invention, the displacing device is configured to influence the direction of displacement of the periosteal tissue as the displacing device is activated.

According to a further feature of the present invention, the displacing device is configured to prevent displacement of the periosteal tissue not in the direction.

According to a further feature of the present invention, the displacing device is configured to take a specific shape as the force inducing mechanism is activated.

According to a further feature of the present invention, the displacing device is configured to grow in a telescopic pattern.

According to a further feature of the present invention, the displacing device is formed at least in part from a stretchable material.

According to a further feature of the present invention, at least part of the periosteal tissue is covered by a rigid structure so as to guide the periosteal tissue to take the shape of the rigid structure as the periosteal tissue is displaced.

According to a further feature of the present invention, the displacing device is formed with at least one fixation feature.

According to a further feature of the present invention, the displacing device is glued to the tissue.

According to a further feature of the present invention, the displacing device is inflatable.

According to a further feature of the present invention the displacing device becomes inflatable after insertion subperiostealy.

According to a further feature of the present invention, the activating is done by turning a screw.

According to a further feature of the present invention, the activating is done by taking an inhibiting component out.

According to a further feature of the present invention, the activating is done by allowing a bio-dissipative inhibiting component to disperse.

According to a further feature of the present invention, the force inducing mechanism comprising magnetic forces.

According to a further feature of the present invention, the movable subperiosteal element is formed at least in part from a magnetic material.

According to a further feature of the present invention, the movable subperiosteal element is enclosed in a biocompatible casing.

According to a further feature of the present invention, the activating is done outside the tissue.

According to a further feature of the present invention, the activating is done inside the tissue.

According to a further feature of the present invention, the force inducing mechanism comprising forces induced by turning a screw.

According to a further feature of the present invention, the screw is hollow and perforated.

According to a further feature of the present invention, the force inducing mechanism comprising a compressed element trying to become not compressed.

According to a further feature of the present invention the force inducing mechanism comprising a distorted elastic element trying to return to its original state.

According to a further feature of the present invention the elastic element comprising a spring.

According to a further feature of the present invention, the compressed element comprising a coil.

According to a further feature of the present invention, the activation is made by a biocompatible material enclosed in a bio-dissipative casing; the biocompatible material becomes active after the casing starts to disperse.

According to a further feature of the present invention, the activation is made by temperature changes.

According to a further feature of the present invention, the movable subperiosteal element is configured so as to allow passage of materials from the periosteal tissue.

According to a further feature of the present invention, the device is configured to allow passage of materials between the exterior space of the device and the interior space of the device.

According to a further feature of the present invention, the displacing device comprising a reference element and the force inducing mechanism induces forces between the reference element and the movable subperiosteal element.

According to a further feature of the present invention, the reference element is fixated to the bone.

According to a further feature of the present invention, the reference element is a bone implant.

According to a further feature of the present invention, the reference element is connected to the movable subperiosteal element by a hinge.

According to a further feature of the present invention, the hinge configured as to allow movement only in one direction.

According to a further feature of the present invention, the reference element is fixated to a tooth.

According to a further feature of the present invention, the reference element is fixated to a dental prosthesis.

According to a further feature of the present invention, the reference element is formed at least in part from magnetic material.

According to a further feature of the present invention, the reference element is gradually displaced.

According to a further feature of the present invention, the reference element includes a ball socket and the force inducing mechanism includes a screw with a ball at its edge; the ball is configured to fit inside the ball socket forming a joint so as to allow control on the position of the screw.

According to a further feature of the present invention, the force inducing mechanism includes forces induced by manual pulling.

According to a further feature of the present invention, the displacing device is a double sheet concave balloon.

According to a further feature of the present invention, the displacing device is configured so as to prevent movement of the movable subperiosteal element towards the bone.

According to a further feature of the present invention, at least part of the displacing device is configured to be pulled out easily from the tissue.

According to a further feature of the present invention, further comprising, prior to inserting the part of the displacing device, forming a subperiosteal tunnel for insertion of the part of the displacing device.

According to a further feature of the present invention, after insertion of the part of the displacing device inside the tunnel, forming a hole in the periosteal tissue above the part of the displacing device and allowing part of the displacing device to protrude above the periosteal tissue.

According to a further feature of the present invention, after insertion of the part of the displacing device inside the tunnel, forming a hole in the periosteal tissue above the part of the displacing device and connecting part of the displacing device to protrude above the periosteal tissue.

According to a further feature of the present invention, the movable subperiosteal element includes a fixation element configured to attach the movable subperiosteal element to the periosteal tissue.

According to a further feature of the present invention, the fixation element is in the shape of an arrow.

According to a further feature of the present invention, the displacing device is used to stabilize a denture.

There is also provided according to the teachings of the present invention, a device for expanding, stretching, displacing or regenerating tissues comprising: a soft tissue displacer for insertion to the bone soft tissue interface and a displacing mechanism configured to displace the soft tissue displacer from the bone so as to create a space between the bone and the soft tissue, the displacing mechanism is configured so the distance between the highest point of the displacing mechanism and the soft tissue is less than the distance between the soft tissue and the bone.

According to a further feature of the present invention the soft tissue displacer is a movable element and the displacing mechanism is a force inducing mechanism configured after activation so as to move the movable element, the movable element is configured after activation of the force inducing mechanism so as to induce forces displacing at least part of the soft tissue.

There is also provided according to the teachings of the present invention, a device for expanding, stretching or displacing bone tissue comprising: a biocompatible movable subperiosteal element for insertion subperiostealy and a force inducing mechanism configured after activation so as to displace the movable subperiosteal element; the movable subperiosteal element is configured after activation of the force inducing mechanism so as to induce forces displacing at least part of the periosteal tissue.

According to a further feature of the present invention, the device is configured to allow the activation to be performed in a plurality of stages separated by at least a number of hours, each stage incrementally displacing the movable subperiosteal element.

According to a further feature of the present invention, the device is configured to allow continuous displacing of the movable subperiosteal element.

According to a further feature of the present invention, the speed of the displacing of the movable subperiosteal element is appropriate for formation of bone callus between the bone tissue and the periosteal tissue.

According to a further feature of the present invention, the force inducing mechanism is a pump.

According to a further feature of the present invention, the device is formed at least in part from a bio-dissipative material.

According to a further feature of the present invention, the device is formed at least in part from a self-expanding material.

According to a further feature of the present invention, the device is configured so as to influence the direction of displacement of the periosteal tissue as the displacing device is activated.

According to a further feature of the present invention, the device is configured to prevent displacement of the periosteal tissue not in the direction.

According to a further feature of the present invention, the device is configured to take a specific shape as the force inducing mechanism is activated.

According to a further feature of the present invention, the device is configured to grow in a telescopic pattern.

According to a further feature of the present invention, the device includes a filling conduit configured for insertion of material beneath the movable subperiosteal element; the filling conduit configured so as to be accessible from outside the periosteal tissue.

According to a further feature of the present invention, the filling conduit includes a one-directional valve.

According to a further feature of the present invention, the filling conduit includes a sealing means.

According to a further feature of the present invention, the filling conduit is comprising a chamber for receiving disinfecting material.

According to a further feature of the present invention, the filling conduit includes at least one fixation component configured to allow fixation of the conduit to the tissue.

According to a further feature of the present invention, the device is formed with at least one fixation feature.

According to a further feature of the present invention, the device is inflatable.

According to a further feature of the present invention, the device is configured so as to become inflatable after insertion subperiostealy.

According to a further feature of the present invention, the movable subperiosteal element is configured so as to allow passage of materials from the periosteal tissue.

According to a further feature of the present invention, the device is configured to allow passage of materials between the exterior space of the device and the interior space of the device.

According to a further feature of the present invention, the device is formed at least in part from a stretchable material.

According to a further feature of the present invention, the device is configured so as to be glued to the tissue.

According to a further feature of the present invention, the force inducing mechanism is configured so as to induce force by turning a screw.

According to a further feature of the present invention, the screw is hollow and perforated.

According to a further feature of the present invention, the device includes an inhibiting component configured to prevent activation of the force inducing mechanism.

According to a further feature of the present invention, the inhibiting component configured so as to be taken out.

According to a further feature of the present invention, the inhibiting component is a wire.

According to a further feature of the present invention, the inhibiting component is formed at least in part from a bio-dissipative material.

According to a further feature of the present invention, the movable subperiosteal element is formed at least in part from a magnetic material.

According to a further feature of the present invention, the movable subperiosteal element is enclosed in a biocompatible casing.

According to a further feature of the present invention, the force inducing mechanism comprising magnetic forces.

According to a further feature of the present invention, the force inducing mechanism comprising a compressed element trying to become not compressed.

According to a further feature of the present invention, the compressed element includes a coil.

According to a further feature of the present invention, the force inducing mechanism includes a material that changes its shape by temperature changes.

According to a further feature of the present invention, the device includes a reference element and the force inducing mechanism configured so as to induce forces between the reference element and the movable subperiosteal element.

According to a further feature of the present invention, the reference element is configured so as to be fixated to the bone.

According to a further feature of the present invention, the reference element is a bone implant.

According to a further feature of the present invention, the reference element is connected to the movable subperiosteal element by a hinge.

According to a further feature of the present invention, the hinge configured as to allow movement only in one direction.

According to a further feature of the present invention, the reference element is configured so as to be fixed to a tooth.

According to a further feature of the present invention, the reference element is configured so as to be fixed to a dental prosthesis.

According to a further feature of the present invention, the reference element is formed at least in part from a magnetic material.

According to a further feature of the present invention, the reference element is configured so as to be gradually displaced.

According to a further feature of the present invention, the reference element includes a ball socket and the force inducing mechanism includes a screw with a ball at its edge; the ball is configured to fit inside the ball socket forming a joint so as to allow control on the position of the screw.

According to a further feature of the present invention, the device is a double sheet concave balloon.

According to a further feature of the present invention, the device is configured so as to prevent movement of the movable subperiosteal element towards the bone.

According to a further feature of the present invention, at least part of the displacing device is configured so as to be pulled out easily from the tissue.

According to a further feature of the present invention, the device includes a protruding element configured so as to be connected to the device after insertion subperiostealy and protrude outside the tissue.

According to a further feature of the present invention, the protruding element is configured to allow connection to other elements.

According to a further feature of the present invention, the protruding element is configured to allow introducing of materials beneath the movable subperiosteal element.

According to a further feature of the present invention, the movable subperiosteal element includes fixation element configured so as to attach the movable subperiosteal element to the periosteal tissue.

According to a further feature of the present invention, the fixation element is in the shape of an arrow.

According to a further feature of the present invention, the device includes an active biocompatible material enclosed in a bio-dissipative casing.

According to a further feature of the present invention the force inducing mechanism comprising a distorted elastic element trying to return to its original state.

According to a further feature of the present invention the elastic element includes a spring.

According to a further feature of the present invention the device includes a mechanism to expand horizontally to reach horizontal diameter larger than the diameter of the hole said device was inserted through.

There is also provided according to the teachings of the present invention a method for expanding, stretching, displacing or regenerating tissues comprising: inserting at the bone soft tissue interface at least part of a displacing device and a displacing element configured to displace the soft tissue displacer from the surface of the bone so as to displace the soft tissue to create a space between the bone and the soft tissue, the device is configured to allow new tissue ingrowth into the space, the soft tissue displacer includes a protruding element rigidly connected to the soft tissue displacer configured to protrude outside the body.

According to a further feature of the present invention the bone is the alveolar ridge and the bone is left open to the oral cavity.

According to a further feature of the present invention the soft tissue displacer is a movable element and the device is configured after activation to move the movable element, the movable element is configured after the activation to induce forces displacing at least part of the soft tissue, the method includes after insertion of the movable element between the soft tissue and the bone activating of the device.

According to a further feature of the present invention the activation is performed in a plurality of stages separated by at least a number of hours, each stage incrementally displacing the soft tissue.

According to a further feature of the present invention the speed of the displacing of the soft tissue is appropriate for formation of bone callus between the bone tissue and the soft tissue.

According to a further feature of the present invention the displacing is combined with introducing a bioactive filling material beneath the movable element.

According to a further feature of the present invention the protruding element is a filling conduit partially inserted into the tissue.

According to a further feature of the present invention the soft tissue is the periosteal tissue.

According to a further feature of the present invention the soft tissue is the Schneiderian membrane of the maxillary sinus or the nose.

According to a further feature of the present invention the displacing element is rigidly connected to the movable element.

According to a further feature of the present invention the activating is done at least partially by turning a screw.

According to a further feature of the present invention the device comprising a distorted elastic element trying to return to its original state.

According to a further feature of the present invention the movable element is configured so as to allow passage of materials from the soft tissue.

According to a further feature of the present invention the device comprising a reference element and the activation is done by inducing forces between the reference element and the movable element.

According to a further feature of the present invention the reference element is fixated to the bone.

According to a further feature of the present invention the reference element is a bone implant.

According to a further feature of the present invention the protruding element is a tube, so the bone implant is at least partially inside the tube.

According to a further feature of the present invention the method further comprising, prior to inserting the part of the displacing device, forming a subperiosteal tunnel for insertion of the part of the displacing device.

According to a further feature of the present invention the device includes a mechanism to expand horizontally to reach horizontal diameter larger than the diameter of the hole the device was inserted through.

According to a further feature of the present invention the soft tissue displacer includes a rigid plate, the plane of the plate substantially parallel the surface of the bone, the height of the device inside the body between the bone and the soft tissue is enlarged as the displacing mechanism is activated.

According to a further feature of the present invention the device is configured not to separate the new tissue from the bone.

According to a further feature of the present invention the movable element includes a semi-rigid part.

There is also provided according to the teachings of the present invention a method for expanding, stretching, displacing or regenerating tissues comprising: inserting at the bone soft tissue interface at least part of a displacing device comprising a soft tissue displacer, the device is configured after activation to displace the soft tissue displacer from the surface of the bone so as to displace the soft tissue to create a space between the bone and the soft tissue, the device is configured to allow new bone tissue ingrowth into the space, without separating the new bone tissue from the bone, the height of the device inside the body between the bone and the soft tissue is enlarged as the device is activated.

According to a further feature of the present invention the activation is performed in a plurality of stages separated by at least a number of hours, each stage incrementally displacing the soft tissue.

According to a further feature of the present invention the displacing is done continuously over a period of time.

According to a further feature of the present invention the displacing device includes a filling conduit partially inserted into the tissue.

According to a further feature of the present invention the displacing device is formed at least in part from a bio-dissipative material.

According to a further feature of the present invention the soft tissue is the periosteal tissue.

According to a further feature of the present invention the soft tissue is the Schneiderian membrane of the sinus or the nose.

According to a further feature of the present invention the displacing device is configured to take a specific shape as the device is activated.

According to a further feature of the present invention the activation of the displacing device is done at least partially by turning a screw.

According to a further feature of the present invention the device comprising a reference element and the activation is done by inducing forces between the reference element and the soft tissue displacer.

According to a further feature of the present invention the reference element is fixated to the bone.

According to a further feature of the present invention the reference element is a bone implant.

According to a further feature of the present invention the soft tissue displacer includes a tube, so the bone implant is at least partially inside the tube.

According to a further feature of the present invention the reference element includes a tube, so the soft tissue displacer is at least partially inside the tube.

According to a further feature of the present invention the device includes a mechanism to expand horizontally to reach horizontal diameter larger than the diameter of the hole the device was inserted through.

According to a further feature of the present invention the soft tissue displacer includes a rigid plate, the plane of the plate substantially parallel the surface of the bone.

According to a further feature of the present invention the movable element includes a protruding element configured to protrude outside the body.

There is also provided according to the teachings of the present invention a device for expanding, stretching, displacing or regenerating tissues comprising: a soft tissue displacer for insertion at least partially to the bone soft tissue interface and a displacing element configured to displace the soft tissue displacer from the surface of the bone so as to displace the soft tissue to create a space between the bone and the soft tissue, the displacing element is configured to allow new tissue ingrowth into the space, the soft tissue displacer includes a protruding element rigidly connected to the soft tissue displacer configured to protrude outside the body.

According to a further feature of the present invention the soft tissue displacer is a movable element and the device is configured after activation to move the movable element so as to induce forces displacing at least part of the soft tissue.

According to a further feature of the present invention the device is configured to allow the activation to be performed in a plurality of stages separated by at least a number of hours, each stage incrementally displacing the soft movable element.

According to a further feature of the present invention the device is configured to allow continuous displacing of the movable element.

According to a further feature of the present invention the device includes a filling conduit configured for insertion of materials beneath the movable element; the filling conduit configured so as to be accessible from outside the body.

According to a further feature of the present invention the activation is done at least partially by turning a screw.

According to a further feature of the present invention the device includes a reference element and the activation is done by inducing forces between the reference element and the movable element.

According to a further feature of the present invention the reference element is configured so as to be fixated to the bone.

According to a further feature of the present invention the reference element is a bone implant and the protruding element is a tube, so the bone implant is at least partially inside the tube.

According to a further feature of the present invention the movable element includes a rigid plate, the plane of the plate substantially parallel the surface of the bone, the height of the device inside the body between the bone and the soft tissue is enlarged as the device is activated.

According to a further feature of the present invention the device is configured not to separate the new tissue from the bone.

According to a further feature of the present invention the device is configured to take a specific shape as the device is activated.

According to a further feature of the present invention the movable element is configured so as to allow passage of materials from the soft tissue.

According to a further feature of the present invention the movable element is a dental implant.

According to a further feature of the present invention the device comprising a distorted elastic element trying to return to its original state.

According to a further feature of the present invention the reference element is a bone implant.

According to a further feature of the present invention the device includes a mechanism to expand horizontally to reach horizontal diameter larger than the diameter of the hole the device was inserted through.

According to a further feature of the present invention the movable element includes a semi-rigid part.

There is also provided according to the teachings of the present invention a device for expanding, stretching, displacing or regenerating tissues comprising: a soft tissue displacer for insertion at least partially to the bone soft tissue interface, the device is configured after activation to displace the soft tissue displacer from the surface of the bone so as to displace the soft tissue to create a space between the bone and the soft tissue, the device is configured to allow new tissue ingrowth into the space without separating the new tissue from the bone, the height of the device inside the body between the bone and the soft tissue is enlarged as the device is activated.

According to a further feature of the present invention the device is configured to allow the activation to be performed in a plurality of stages separated by at least a number of hours, each stage incrementally displacing the soft tissue displacer.

According to a further feature of the present invention the device includes a filling conduit configured for insertion of materials beneath the soft tissue displacer; the filling conduit configured so as to be accessible from outside the body.

According to a further feature of the present invention the activation is done at least partially by turning a screw.

According to a further feature of the present invention the device includes a reference element and the device is configured so as to induces forces between the reference element and the soft tissue displacer.

According to a further feature of the present invention the reference element is configured so as to be fixated to the bone.

According to a further feature of the present invention the reference element is a bone implant and soft tissue displacer includes a tube protruding outside the body, so the bone implant is at least partially inside the tube.

According to a further feature of the present invention the soft tissue displacer includes a rigid plate, the plane of the plate substantially parallel the surface of the bone.

According to a further feature of the present invention the device is configured to take a specific shape as the device is activated.

According to a further feature of the present invention the soft tissue displacer is configured so as to allow passage of materials from the soft tissue.

According to a further feature of the present invention the soft tissue displacer is a dental implant.

According to a further feature of the present invention the screw is hollow and perforated.

According to a further feature of the present invention the reference element is a bone implant.

According to a further feature of the present invention at least part of the device is configured so as to be pulled out easily from the tissue.

According to a further feature of the present invention the device includes a mechanism to expand horizontally to reach horizontal diameter larger than the diameter of the hole the device was inserted through.

According to a further feature of the present invention the reference element includes a tube, so the soft tissue displacer is at least partially inside the tube.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
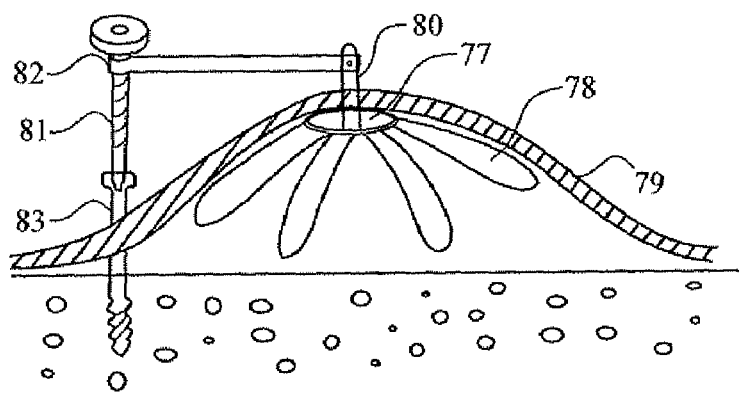
FIG. 1 is a perspective view illustrating the novel device for displacing the gums with an external screw.

As mentioned further above there are many implementations of the invention in different areas of the body. The following description will focus on embodiments for regenerating bone in the mandible and in the maxillary sinus in order to understand the principles of the devices and methods. The same principles should be used in other areas of the body.

Before turning to the features of the present invention in more detail, it will be useful to clarify certain terminology as will be used herein in the description and claims, It is noted that a large number of different types of materials are known which may be inserted within the body during a surgical procedure and which later dissipate, thereby avoiding the need for a separate surgical procedure for their removal. Such materials are properly referred to, depending upon the mechanism by which the material dissipates, as "bioresorbable", "bioabsorbable" or "biodegradable". Despite the differences between these different classes of materials, the aforementioned terminology is widely used interchangeably by medical professionals. Accordingly, and for conciseness of presentation, only one of these terms will generally be used in the following description, without implying the exclusion of the other classes of materials. Additionally, the phrase "bio-dissipative material" is used herein in the description and claims to refer generically to any and all materials which dissipate without requiring surgical removal, independent of which mechanisms such as dissolution, degradation, absorption and excretion take place. The actual choice of which type of materials to use may readily be made by one ordinarily skilled in the art, and is not generally essential to the present invention.

The term "magnetic material" is used herein to refer to a magnet or materials that are attracted by a magnet.

In the following descriptions the invention will be demonstrated on the mandible therefore the bone is down and the periosteal tissue and the gums are up. Beneath the periosteal tissue means between the bone and the displaced periosteal tissue.

Finally with respect to terminology, reference will be made to a biocompatible filling material used to fill the inflatable elements of the present invention. It should be noted that this filling material may assume a wide range of compositions and consistencies, so long as the biocompatible material may be forced into the inflatable element. Thus, possible consistencies for the filling material include, but are not limited to, consistencies described as watery, viscous, gelatinous, moldable, waxen, particulate, and suspensions or mixtures combining any of the above. The term bone augmenting material or tissue augmenting material means a material that assist in the regeneration of the tissue or the bone. Preferably the bone augmenting materials are bio-dissipative materials that occupy a space in the body for several months and encourage the adjacent bone tissue to grow inside this space and replace the bone augmenting material. The bone augmenting materials can be also non-resorbable and serve for aesthetic or mechanical purpose.

Turning now in detail to the drawings, which depict the presently preferred embodiments of the invention for the purpose of illustrating the practice thereof and not by way of limitation of the scope of the invention, and in which like reference characters refer to corresponding elements throughout the several views. FIG. 1 illustrates a basic device embodying the present invention for use in bone reconstruction and, in particular, for augmentation of atrophic alveolar ridges. The device based on external screw is composed of displacing element in the shape of a plate 77 preferably the plane of the plate substantially parallel the surface of the bone with projections 78 located beneath the gums 79 subperiosteally and a small bar 80 that is protruding outside the tissue preferably rigidly connected to the plate 77. Preferably the plate 77 and the bar 80 are one piece. This bar 80 is connected to a screw 81 by a nut 82. The screw is placed on a stable bone implant 83. When the screw is turned the plate is moving upwards and displacing the gums. The space beneath the gums, which is surrounded by bone from one side and by soft tissue from all the other sides, will be filled with materials from the surrounding tissue and will become bone. It is important to do the displacing slowly to allow the regeneration of the gums and also to allow the formation of a bone callus. The recommended rate is 0.5-1.5 mm a day. The shape of the plate 77 and the projections are designed to allow passage of materials and blood supply from the periosteal tissue to the space developing beneath the plate 77 and projections 78 which is important for regeneration of bone. It is also important to block the passage of materials and bacteria from the oral cavity to the same space. Therefore the plate is not perforated. Any configuration of the displacing element that will have a sealed area close to the part projecting outside the gums and a perforated area distant from this projecting area will function the same. The projections are preferably semi-rigid or elastic so they can bend and not to perforate the gums at their edges.

The device preferably includes some stabilizing elements to prevent micro-motion of the plate 77 in respect to the bone. The device preferably will have a stabilizing element in the connection of the nut 82 to the screw 81 and in the connection of the screw 81 to the bone implant 83. Micro-motion is movement of several dozens of microns that can interfere with the process of bone formation.

The device can be placed by raising the periosteal tissue, placing the device on the bone and suturing the periosteal tissue on top of the device. In another embodiment the gums are perforated to allow the projecting part 80 to protrude to the oral cavity. In these techniques activation can start several days after the insertion to allow the place of the sutures to heal. An improved technique is to create a sub periosteal tunnel insertion of the displacing device into the tunnel and perforating the gums above the displacing device to allow the projecting part to protrude to the oral cavity. In this technique activation can be done immediately after insertion since there are no sutures in the periosteal tissue to be displaced. There are some sutures only at the opening of the tunnel, which is distant.

Figure 2A:
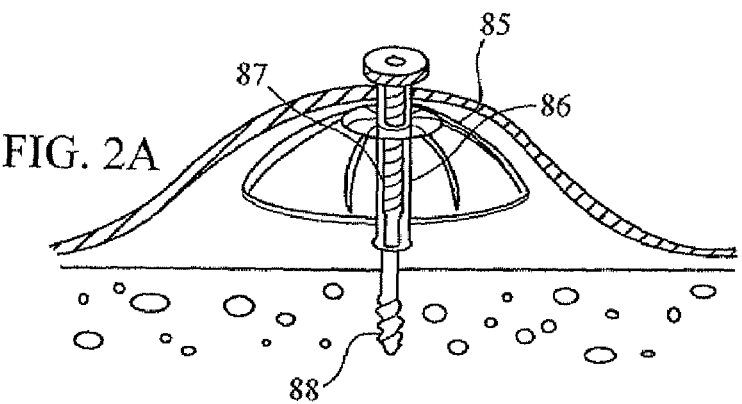
FIG. 2A is a perspective view illustrating the novel device for displacing the gums with an internal screw.
Figure 2B:
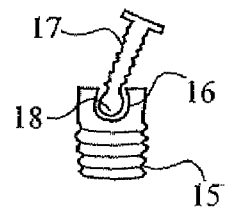
FIG. 2B is a sectional view illustrating a bone implant with a ball socket to control the position of the screw that is moving the displacing element.

In another preferred embodiment based on internal screw illustrated in FIG. 2B the displacing element 85 is in the shape of a dome with a tube 86 in the center protruding outside the tissue. The tube 86 is preferably rigidly connected to the displacing element 85. The tube has threads compatible with a screw 87 coming from outside the tissue and standing on a bone implant 88. When the screw is turned the dome with the tube is moving upwards and displacing the gums. The advantage of this technique is that only the tube 86 and the screw 87 are protruding to the oral cavity instead of all the activation mechanism of FIG. 1 that includes the bone implant 83, the screw 81, the protruding element 80 and the connection between them as illustrated in FIG. 1. As the protruding element is bigger it is more uncomfortable to the patient. The tube preferably has a sealing means to prevent bacteria to penetrate below the periosteal tissue. Preferably the screw 87 is completely inside the tube and only the tube 86 is in contact with the oral cavity. Before activating the device the sealing means is detached from the tube, the screw 87 is turned and the sealing means is placed again.

The edges of the displacing element are rounded to prevent perforating of the gums. The displacing device can be made from titanium or any other biocompatible material like silicon. The plate can be made from combination of materials like titanium at the area close to the protruding element and semi-rigid silicon at the borders of the displacing device. The borders of the displacing element can be also covered by a guided bone regeneration membrane made of P.T.F.E. or collagen or any other biocompatible polymer. If the borders of the displacing element are made of a softer material they will not perforate the gums. The displacing element is preferably semi-rigid with a softer material at its edges. The displacing device is preferably rigid like titanium near the protruding element, semi-rigid like silicon or rubber around the rigid area and preferably soft like a cloth t its borders. The guided bone regeneration membrane can cover the displacing element and to touch the periosteal tissue preferably except for the region near the protruding element. The guided bone regeneration membrane can be folded and reach the bone and to unfold as the displacing element is elevated. The plane of the displacing element is preferably substantially parallel the surface of the bone at the crest of the alveolar ridge.

The device of FIG. 2A preferably includes stabilizing elements like nuts to prevent micro motion of the displacing element in respect to the bone.

In another preferred embodiment illustrated in FIG. 2B the bone implant 15 can include a ball socket 16 and the screw 17 include a ball 18 at its edge to form a joint therefore allows the control on the position of the screw and the direction of the displacement.

Figure 3:
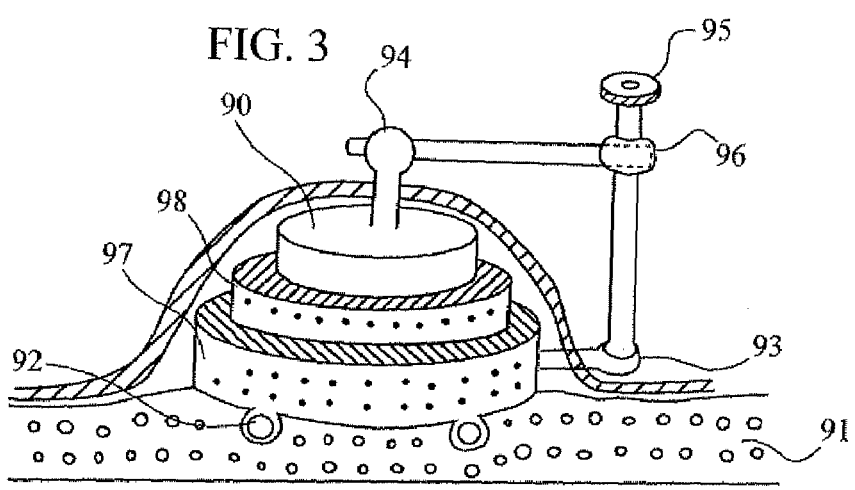
FIG. 3 is a perspective view illustrating the novel device for displacing the gums with a telescopic form.

In another preferred embodiment the device can be configured to expand in a pre-designed direction and take a specific shape as it grows. For example the device can be designed in a telescopic configuration as illustrated in FIG. 3. A hollow cylinder 97 is fixated to the bone 91 by fixating screws 92. It can be also fixated by nails pushed inside the bone or glued to the bone by bone cements like calcium sulphate. Inside the hollow cylinder 97 there is a container 90 with a smaller diameter, which is open towards the bone. Between the hollow cylinder and the container one or several hollow cylinders 98 can be. There are two projections from the telescope. One 93 protrudes from the lower hollow cylinder to the side and terminates in a base for a screw. This one can be outside the tissue as in FIG. 3 or can be inside the tissue. The second projection 94 is a bar that is protruding from the container upwards. This bar is connected to a screw 95 by a nut 96. The screw 95 is placed on the base for a screw 93. When the screw is turned the upper cup of the telescope is moving upwards and displacing the gums. The walls of the telescope are perforated to allow materials from the tissue to go inside the telescope. The base of the telescope is the bone so after fixating the telescope to the bone the telescope becomes inflatable. It is also possible to attach a filling conduit to the telescope to allow the insertion of materials that enhance the growth of bone tissue. The filling conduit is preferably filled with bone augmenting material in gelatinous consistency or suspension. The filling material can be an autograft, an allograft, a xenograft, an alloplast, a cytokine, a hormone, a growth factor, a physiologically acceptable drug, a biological modifier, a protein, an antigen, a cell chemotaxis stimulator material, a material inducing osteogenesis, an osteoinduction material, an osteoconduction material, a bioactive material, a bioresorbable material, a bioabsorbable material, a biodegradable material and any combination thereof. The filling material can be augmenting bone material available in the market like hydroxyapatite, bovine mineral (i.e. Bio-Oss available from Geistlich, Swiss), demineralized freezed dried bone, synthetic materials like PLA (i.e. Fisiograft from Ghimas, Spain). The filling material can be also fully or partially not bioresorbable if the procedure is done only for aesthetic reason and implants are not going to be inserted, for example crystal hydroxyapatite.

The filling material can include therapeutic materials and can include self-expanding materials from the list mentioned above. Many of the bone augmenting materials have the tendency to expand when getting wet by hydration.

Figure 4A:
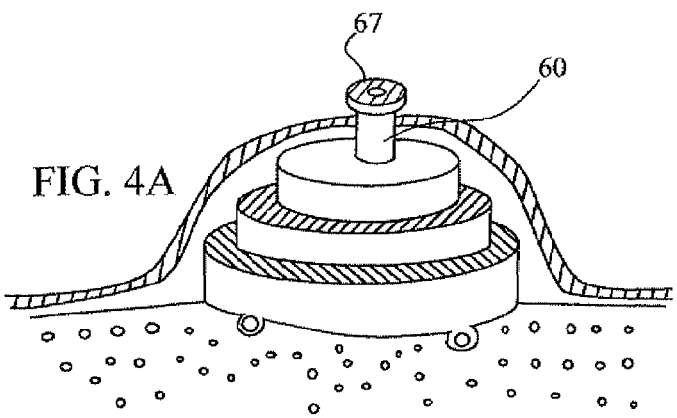
FIG. 4A is a perspective view illustrating the novel device for displacing the gums using an inflatable telescope.

Another preferred embodiment, of an inflatable device that resembles the device of FIG. 3 is illustrated in FIG. 4A. The protruding part is a filling conduit 60 preferably connected to the telescope by screwing. The displacing is done by introducing a biocompatible material inside the device. The filling conduit is made of a biocompatible material and can be made from more then one type of material bioresorbable or non-bioresorbable. Preferably the filling conduit is a cannula made of commercially pure titanium or titanium alloy used in the dental implant industry. The cannula is connected to the device in one side and in the other side it can be filled and closed with a screw 67 as a sealing component. Sealing components can be also a valve, a clamping element, a knot and combination thereof. The conduit can have variable shapes, dimensions, cross section and elasticity. The filling is preferably by using a syringe that is screwed to the cannula. The cannula can have preferably fixating components in order to prevent the cannula from moving, get out and cause uncomfortable filling to the patient. The a fixation component can be selected from the group consisting of hook, hole for sutures, slot, thread, bulge, screw, change in dimension, irregularity and any combination thereof.

Figure 4B:
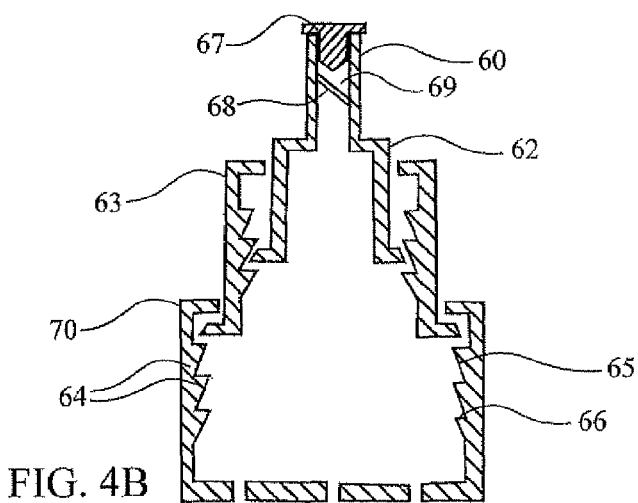
FIG. 4B is a sectional view illustrating the novel device for displacing the gums using an inflatable telescope.

The telescopic design allows to control the shape and the direction of the displaced periosteal tissue. The filling material prevents the collapse of the telescope. The telescope can have a base made from a bioresorbable material. It can be made from autograft, allograft, xenograft and alloplast and combination thereof. Preferably, the resorbable part is made of conventionally available polyglycolic acid (PGA) mesh, a high-molecular-weight linear polymer made by the ring opening polymerization of the purified glycolide monomer, although other suitable materials might be used e.g. polyglactin 910, i.e. polyglycolide co-galactide. In addition, collagen or PDS (another absorbable suture material) or cellulose might possibly also be used. The base can be also made from stiff bioresorbable materials like polylactic acid (PLA). The base is preferably has little holes to allow the penetration of bone cells. The rest of the device is preferably made from titanium. FIG. 4B is a cross section of the device of FIG. 4A. The parts of telescope are configures so the diameter of the upper region of a lower part is narrower than the diameter of the lower region of the higher part. Therefore when pulling the small container 62 upwards towards the gums till it's lower region will reach the upper region of the adjacent hollow cylinder 63 it will pull the adjacent hollow cylinder 63 upwards. Each hollow cylinder in this way will pull the next one resulting in a higher and bigger compartment with a pre designed shape. The walls can have small projections 64 on their inner side that allow only upward movement. The projections can have an incline on their lower part 65 and horizontal plane in their upper part 66. This configuration prevents changes in the shape of the device as a result of forces coming from the gums. The filling conduit 60 preferably can include a screw 67 for sealing, a one directional valve 68 and chamber 69 between them for containing disinfecting material to prevent penetration of bacteria inside the telescope. This disinfecting material preferably a biocompatible antiseptic material like chlorhexedine gel or calcium-hydroxide. The antiseptic material should be washed out before filling and put again when the cannula is closed. While introducing the biocompatible materials preferably materials that enhance bone regeneration the telescope can be pulled up manually to reduce the pressure needed for insertion of the material. In another preferred embodiment a screw is connecting the small container 62 and the lower part 70 like the screw in FIG. 3 that can also help to reduce the pressure needed for insertion of the material. The device can include also self-expanding components or materials that expand in humidity or in body temperature. Materials include, either alone or in combination, metals or metal alloys, polymers, carbon and ceramics. Exemplary metallic members include stainless steel, titanium, tantalum, shape-memory materials such as nickel-titanium alloy (NiTi) (Compounds using NiTi are manufactured under the marks NITINOL™ and ELASTINITE™ and are available from several sources), Elgiloy (trade name) and NP35N (trade designation), which can provide desired degree of springiness, malleability and/or response to temperature changes. Exemplary polymers include polyurethanes, silicon rubbers, polyether sulfones, fluoroelastomers, polyimides, polycarbonates, polyethylens, polylactic acid, polyglycolic acid, polyacrylates, and the like and combinations and copolymers thereof which provide a variety of abilities to bioabsorb or biodegrade or to be totally inert. The device can include springs and coils that are compressed before insertion and can include stretchable and elastic materials for example polyurethanes like polycarbonate urethane.

After finishing the filling process the cannula is preferably taken out and a low screw is place instead and the gums are sutures above the device. This is done to prevent infection through the cannula.

Figure 4C:
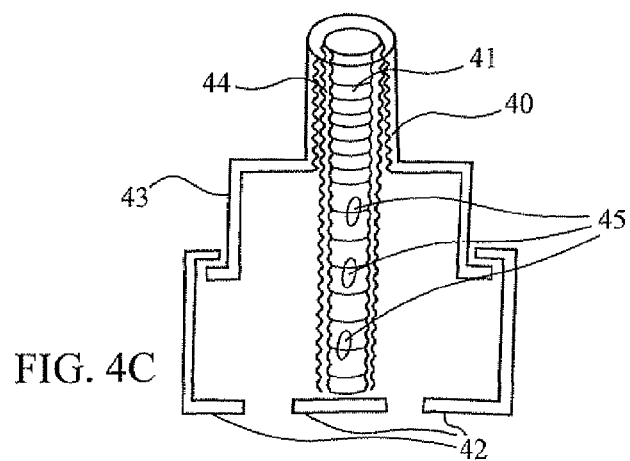
FIG. 4C is a sectional view illustrating the novel device for displacing the gums using an inflatable telescope and a hollow perforated screw for enlarging the telescope and for insertion of materials inside the telescope through the screw.

In another embodiment illustrated in FIG. 4C the cannula 40 has internal threads and a perforated hollow screw 41 can be screwed to the cannula. The screw 41 is touching the base 42 of the telescope and when activated the upper part of the telescope 43 is moving upwards. This hollow screw 41 has preferably threads 44 on its inner aspect to allow connection with a syringe. So by turning the hollow screw the telescope is growing and bone-regenerating material can be easily introduced inside the telescope. This hollow screw 41 can be left inside to prevent the upper part 43 from moving toward the bone. This hollow screw can be sealed with a screw on its inner threads. The hollow screw has holes 45 in its walls to allow the bone regenerating material to get out of the hollow screw and get inside the telescope.

In all the embodiments described the device preferably includes a stabilizing element to prevent micro-motion of the device in respect to the bone and preferably the borders are covered by a softer material.

Figure 5:
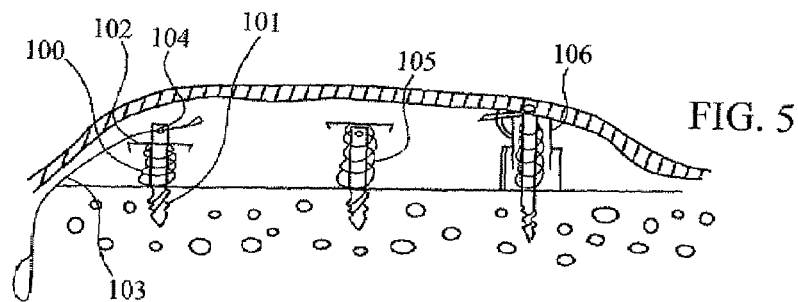
FIG. 5 is a sectional view illustrating the novel device for displacing the gums using coils.

In another embodiment based on a coil and a wire as inhibiting component illustrated in FIG. 5 a compressed coil 100 attached to a bone implant 101 is placed beneath the gums. The coil is compressed by a small plate 102 placed on the bone implant. The plate is not moving because a wire 103 is placed above the plate through a hole 104 in the bone implant and protruding outside the tissue. After the tissue is healed from inserting the implants the wire is pulled out resulting in releasing of the coil 105 and displacement of the tissue. The coil can be inside a telescope 106.

Figure 6:
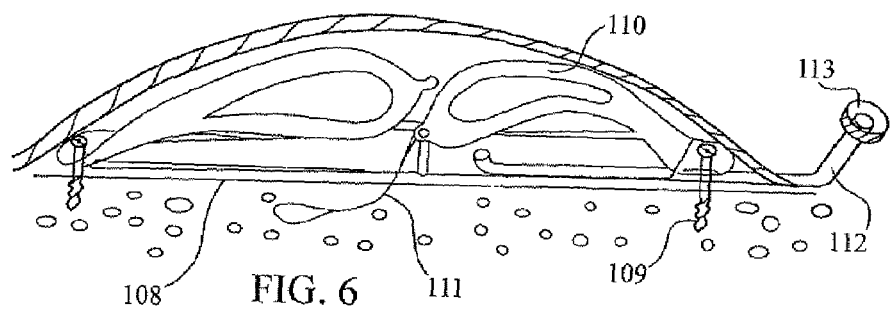
FIG. 6 is a perspective view illustrating the novel device for displacing the gums using bended rings.

In another embodiment illustrated in FIG. 6 the displacing element is composed of a large elongated ring 108 placed on the bone and fixated to the bone by screws 109. From the corners of the ring two elongated small elastic rings 110 are emerging. The angle between the large ring and the small ring is close to 90 degree when the device is passive. Before insertion of the device inside the tissue the free corners of the rings are pulled toward the large ring by a wire 111 protruding outside the tissue. When the wire is pulled out the rings try to move upwards and displace the tissue. The wire can be made from bioresorbable material therefore no need for pulling out the wire. A conduit 112 is preferably attached to the large ring and protruding outside the tissue to allow insertion of materials that promotes the growth of the bone tissue. The conduit preferably has a sealing component 113. Another preferred embodiment can use a device that the filling element for example the cannula is made of two parts one is external made of nonresorbable material and the second is internal made of bioresorbable material. The border between the two is preferably the slot. In this device it is easy to take the nonresorbable part out by twisting the cannula and leaving the bioresorbable inside the body.

Figure 7:
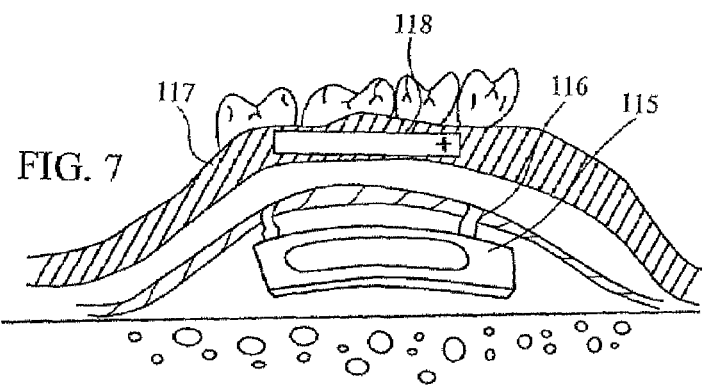
FIG. 7 is a perspective view illustrating the novel device for displacing the gums using a magnetable metal beneath the gums and a magnet inside a denture.
Figure 24:
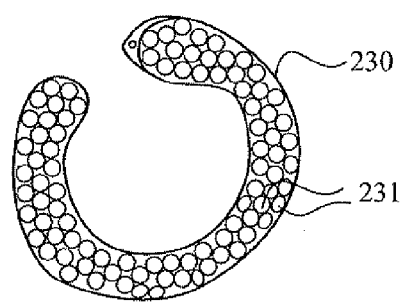
FIG. 24 is a prospective view demonstrating an implant for the breast to allow magnetic tissue expansion.
Figure 25:
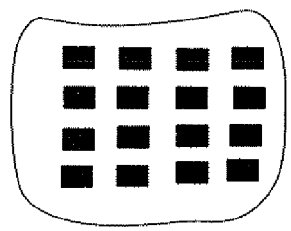
FIG. 25 is a prospective view demonstrating an implant to be used bellow the skin to allow magnetic tissue expansion.

In another embodiment illustrated in FIG. 7 the displacing element is a magnet or a metal attracted to a magnet enclosed by a biocompatible material 115. The magnet is placed beneath the gums preferably using the tunnel technique. This metal 115 preferably fixated to the gums by sutures 116 or by projecting small arrow 120 that penetrate the tissue. This displacing element is preferably perforated to allow passage of materials from the periosteal tissue. Over the gums a denture 117 is fabricated to have a space above the gums. Inside the denture a magnet 118 is inserted so to attract the magnetable metal beneath the gums. The patient is instructed to wear the denture resulting in displacement of the gums. This method can also help to stabilize a denture without the displacement of the tissue. The magnet should be placed 1 mm above the gums and gradually pulled upwards as the gums are getting close to the magnet. Preferably the magnet is connected to a screw or a wire to allow easy displacing of the magnet. This method allows the periosteal distraction to be operated without anything projecting from the gums therefore the chances for infection are reduced. This method also allows the process to be done without manipulation inside the patient mouth. The shape of the space in the denture above the magnetable metal will dictate the shape of the periosteal tissue after displacement. The method of tissue expansion using a magnet is not limited to the periosteal tissue. These methods and devices can be used with some modification of soft tissue regeneration in other areas of the body. For example breast augmentation can be done by inserting bellow the skin of the breast a magnetic material in a biocompatible and the women is wearing a bra that has a magnetic structure inside. The shape of the magnetic implant, its location in the breast and the location of the magnetic structure in the bra are according to the desired augmentation. The magnetic structure is designed to be close to skin because the magnetic forces are dependent on the distance between the objects. The magnetic structure is designed to allow gradual displacement of the structure inside the bra so every day or several days the structure is displace about 1 mm and the magnetic implant is pushing the skin of the breast towards the magnetic structure. The use of a set of bras with gradual size enlargement can be also used. This process of expanding the skin of the breast will cause skin regeneration like a regular tissue expander. The new volume in the breast will be filled with new tissue that can be glandular tissue, connective tissue or fat tissue. The end result is enlarged breast that has new natural tissue inside instead of silicon implants that are used today for breast augmentation. Silicon implants are known to cause hard scar tissue around them which are not comfortable. Silicon implants are also suspected of causing breast cancer. Preferably the implant is designed to be eventually easily taken out. The implant can be perforated to allow good blood supply to the skin above the implant. In most cases the best location for placing the implant is bellow the areola which is the dark area around the nipple. Preferably the implant is inserted in a minimal invasive manner through a small incision. To allow the placement of the implant inside the breast around the nipple without damaging the glandular tissue and the ducts the implant is preferably in the shape of an open circle as illustrated in FIG. 24. The implant is preferably flexible to allow its positioning around the glandular tissue. The implant is also preferably soft to prevent uncomfortable filling to the patient. One preferred embodiment is as illustrated in FIG. 24 a circular tube 230 made of silicon or any other biocompatible material and inside many small balls 231 of magnetic material. This configuration is flexible and soft and can be easily placed around the glandular tissue through a small opening and also can be easily taken out. In some other cases lifting the upper region of the breast is needed in these cases an implant in a sheet like appearance is inserted bellow the skin in the upper region of the breast and the magnetic structure in the bra is placed above this region. The implant is made from magnetic material and closed in a biocompatible cover. The implant can be perforated as illustrated in FIG. 25 and can have inside also small magnetic balls as in FIG. 24. These devices can be use just for skin regeneration like regular tissue expanders in every region in the body like the head and the magnetic structure is inside a hat and in other places in the body and the magnetic structure is in the clothes. The advantage of magnetic tissue expander over a regular tissue expander except for the inner tissue regeneration is that the patient doesn't have a canulla getting outside the body which is not comfortable and also can lead to infection. The excess of skin can help in plastic surgery for skin transplantation, augmentation and hair transplantation.

Figure 8:
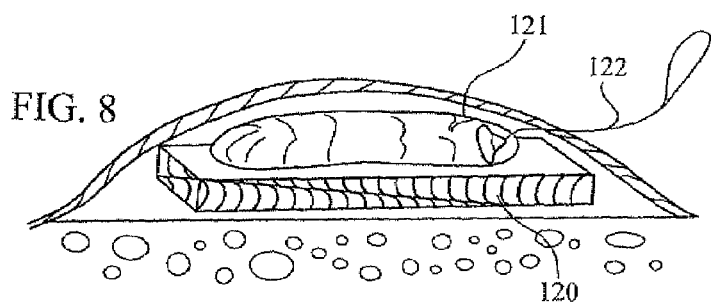
FIG. 8 is a perspective view illustrating the novel device for displacing the gums using a self-expanding material.

In another embodiment illustrated in FIG. 8 the displacing element is composed of a plate 120 preferably made from stiff bioresorbable material. On top of the plate there is a material like poly (dioxanone-co-glycolide) and on top of it a catalyst enclosed in a casing 121. The casing is attached to a wire 122 allowing the puling of the casing and releasing of the catalyst. In another preferred embodiment, the casing can be made from a bioresorbable material. When the catalyst is in contact with the material in the plate a polymerization reaction starts with expansion and release of $CO_2$. This expansion will displace the tissue. This material is also used as a bone substitute material.

Figure 9:
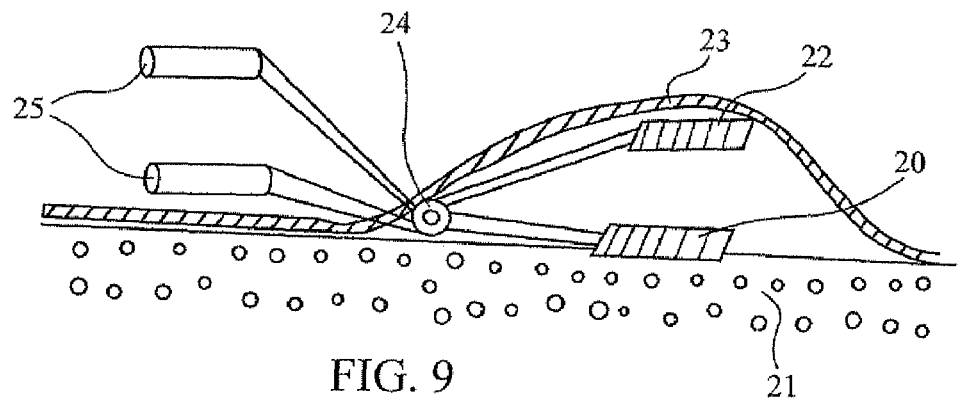
FIG. 9 is a perspective view illustrating the novel device for displacing the gums using a hinge.

In another preferred embodiment illustrated in FIG. 9 the device is made from two parts placed subperiostealy. One is a reference part 20 touching the bone 21 and the second one is a displacing element 22 touching the periosteal tissue 23. The displacing element is preferably perforated. The two parts are connected with a hinge 24. The hinge preferably allows movement only in one direction to prevent collapse of the periosteal tissue. Both parts have projections 25 outside the tissue that are configured to be attached to an external instrument. The external instrument when activated works like scissors and causing the subperiosteal element to move upwards. This displacing device can easily be pulled out from the tissue at the end of the procedure.

Figure 10:
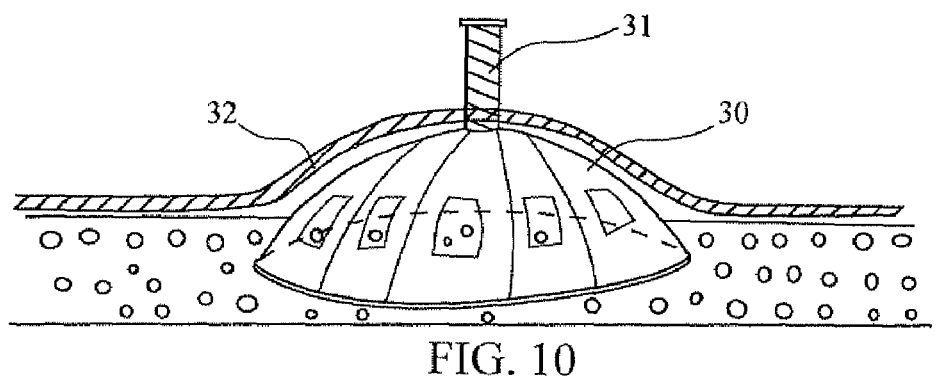
FIG. 10 is a perspective view illustrating the novel device for displacing the gums using an inflatable double sheet balloon in the shape of a dome.

In another preferred embodiment illustrated in FIG. 10 the displacing device is a concave double sheet balloon 30 connected to a cannula 31. The balloon 30 is placed subperiostealy and the cannula 31 is projecting outside the periosteal tissue 32. When the balloon is inflated it takes the shape of a dome that is perforated and the periosteal tissue 32 is elevated. The balloon can be connected to a pump therefore no need for several treatments in some hours intervals instead the inflation is continuous.

Figure 11A:
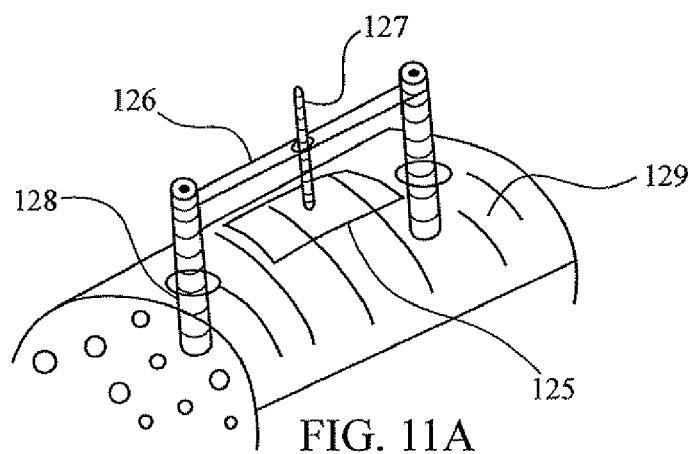
FIG. 11A is a perspective view illustrating the novel device for displacing the gums using a rigid element above the gums and a screw or a spring pulling the plate beneath the gums.
Figure 11B:
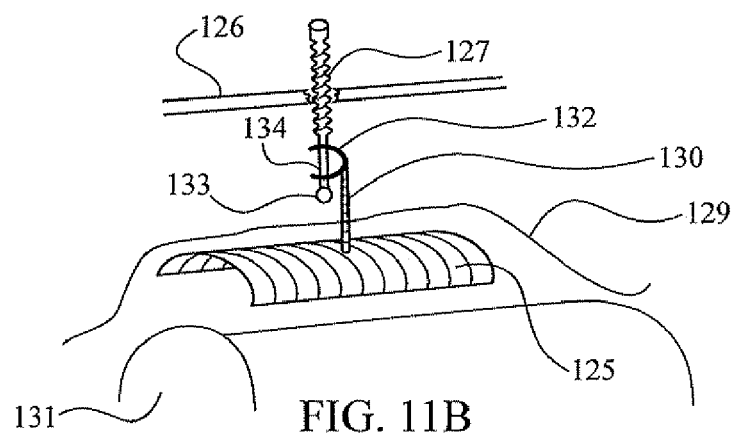
FIG. 11B is a perspective view illustrating the connection between the elevating screw and the plate configured to allow replacement of the screw.

In another embodiment illustrated in FIG. 11A the force inducing mechanism can pull up a plate 125 for example by fixating a rigid element 126 several millimeters above the gums 129 and a screw 127 is passing through threads in the rigid element 126 and connects to the plate 125. The connection is configured to allow rotation of the screw 127 without rotation of the plate 125. The rigid element can be fixated by connecting to temporary dental implants 128 or to natural teeth. The rigid element can be a temporary bridge. When rotating the screw 127 the plate 125 is elevated. The problem is that the screw 127 is also elevated so if the rigid element 126 was several millimeters above the gums 129 now the top of the screw 127 is several millimeters above the rigid element 126 and probably this device will be suitable only to cases when there are no antagonist teeth. In a preferred embodiment illustrated in FIG. 11B the plate 125 which is preferably rounded to resemble and substantially parallel the morphology of the alveolar ridge 131 (The bended morphology of the plate is preferred for all the embodiments) includes a projection 130 configured to allow connection to the screw 127 so the screw can be easily disconnected and replaced with a shorter screws so the upper region of the forced inducing mechanism, in this case the top of the screw 127, is elevated less than the plate 125. This kind of connection can be for example if the projection 130 has an open ring 132 at the upper edge of the projection 130 and the screw 127 has a ball 133 at the lower edge of the screw. The ball is connected to the screw by a narrow neck 134. The diameter of the narrow neck 134 is less than the diameter of the opening in the open ring 132 therefore the narrow neck can be inserted through the opening in the open ring inside the open ring 132 an can be taken out and replaced. The diameter of the ball 133 is larger than the inner diameter of the open ring 132 therefore when the screw is elevated it pulls the projection 130 and the plate 125. In this preferred embodiment as well in all the other embodiments of this invention the height between the level of the most upper region of the force inducing mechanism at the end of the elevation and the level of the movable element at the beginning of the elevation is less than the elevation of the movable element plus the height between the level of the most upper region of the force inducing mechanism and the level of the movable element at the end of the elevation. In other wards the basic principal of the present invention is a device for insertion between the bone and the adjacent tissue that includes a soft tissue displacer preferably in the shape of a bended plate and a displacing mechanism to control the distance of the soft tissue displacer from the bone. The device is configured so after the final displacement the distance between the most upper region of the displacing mechanism and the soft tissue is less then distance between the soft tissue and the bone (If the device is completely beneath the soft tissue then the distance between the most upper region of the displacing mechanism and the soft tissue is negative). In all the embodiments the plate preferably is stabilized to prevent micro-motion and the plate is semi rigid or preferably has soft borders.

In another preferred embodiment the plate of FIG. 11A is elevated by a spring instead of a screw. The spring is connected between the rigid element and the plate. The use of a spring eliminates the need for several appointments and reduces the "chair times".

Figure 12:
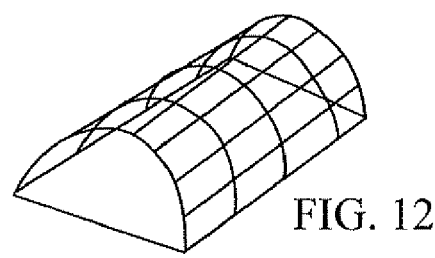
FIG. 12 is a perspective view illustrating the novel device for displacing the gums using a flexible mesh.

In another preferred embodiment illustrated in FIG. 12 the device is in the shape of a half of a tube. The device is preferably made from a mesh of biocompatible metal fibers like titanium or stainless and the mesh is flexible. The device preferably includes fixation elements to allow fixation of the device to the bone. The device is placed so the concave region of the half tube is facing the bone and the convex region is facing the gums. The device can be fixated by screws or tacks. The device is inserted and the gums are sutured above the device so the device is compressed and touching the bone. Gradually the mesh expands to reach the original shape of a half tube and therefore displacing the gums and creating a space beneath the device. In another embodiment the device can be in the shape of a full tube made from a mesh of titanium fibers resembling the structures of a stent that can be easily compressed to form a narrow tube and is trying to form a wider tube. This device will function as the previous device but after the bone is regenerated it will be very difficult to take it out. This device since it is made from biocompatible metal like titanium can stay and the dental implants can be inserted through the device. These devices and the devices described above preferably are inserted using the tunnel technique.

Figure 13:
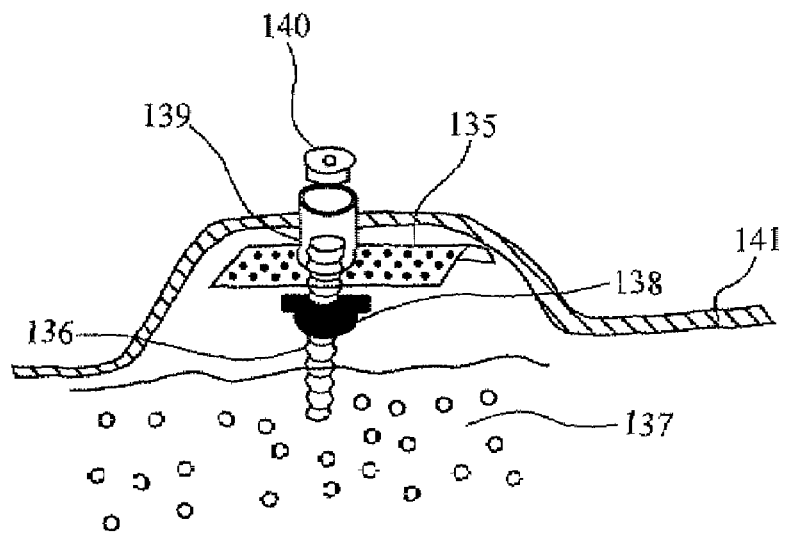
FIG. 13 is a perspective view illustrating the novel device for displacing the gums using a dental implant and a nut.

In another preferred embodiment illustrated in FIG. 13 the device is made from three parts the upper part facing the gums is a movable element preferably in the shape of a plate 135 made from a rigid material like titanium or a rigid bio-dissipative material or at least partially from a semi rigid material like silicon. The plate is preferably rounded and perforated and is preferably rough especially on its edges to strengthen the connection between the plate 135 and the gums 141. The distraction can be done by an elevating mechanism for example a mechanical elevating mechanism like an elevating screw 136. The elevating screw 136 is fixated to the bone 137 and an elevating nut 138 is threaded on the elevating screw 136. The elevating screw 136 can be partially inserted into the bone 137 and to protrude above the bone. The elevating screw can be self-tapping so it can be inserted even without drilling. The elevating nut 138 is configured to displace the upper plate 135 and consequently. displacing the gums 141. In this embodiment the elevating screw 136 helps also in stabilizing the plate 135 and in controlling the direction of displacement. The elevating screw 136 as mentioned can be hollow and perforated and can be a bone implant or the final dental implant. In the embodiments that the screw is configured to be the final dental implant, it is recommended that the screw will not be in direct contact with the oral environment, in order to keep the properties of the surface of the bone implant. In these embodiments the plate can include a tube 139 that can be sealed with a sealing cup 140. The elevating screw 136 is placed in the space of the tube 139 and activating the nut 138 is done through the tube 139. Preferably the sealing cup is threaded to the elevating screw 136 so it forces the plate 135 to the nut 138 and stabilizes the plate to prevent micro-motion. Filling the space beneath the plate with bone augmenting material can be through the screw if it is hollow or through another opening in the plate. Preferably the tube 139 has on its upper region signs like small projections or slots or stripes to show its relation to the plate. The relation to the plate is important because the dentist can't see the plate and therefore can't be sure if the plate is not rotated also. The dentist can see only the tube so if the tube has signs showing the orientation of the tube the dentist can verify the position of the plate before stabilizing the plate. If the plate is rotated it can push the gums and perforate them. In another preferred embodiment a device like the device described above has more then one elevating screw. The plate is like the previous plate of but is more elongated. There are two elevating screws, two nuts, two tubes and two sealing cups. This embodiment is recommended for the augmentation of edentulous ridge. The use of more then one elevating screw improves the stabilization of the device and prevents the rotation of the upper plate when activating the elevating nuts. It is recommended that the tubes will be made of titanium, the plate can be made from titanium or semi-rigid material and also to have softer material like P.T.F.E. at its borders. The screws are preferably hollow and perforated. The screws are inserted by using a parallelism guide. After the screws are inserted the nuts are placed over the screws and threaded to be adjacent the bone. Then the plate is placed over the screws and nuts. The tubes can be sealed by using sealing cups. The sealing cups can be threaded to the tubes if the tubes have threads in their upper region or preferably to the screws 136. At the beginning the sealing cups are high and should be replaced with lower cups as the plate is displaced. It is recommended to displace vertically the plate at a rate of 1 mm per day. The displacement of the movable elements like the plates described here, above and later, can be done in several steps or continuously over a period of several hours or days. The continuous manner can include a pump for continuous filling of the device and a mechanical or electrical component that exerts forces for a long period of time. After the movable element has reached its final location and the space beneath the movable element is preferably filled with bone augmenting material, it is possible to add bio-active materials into the device even several weeks and months later. Bio-active material can be Bone Morphogenic Proteins (B.M.P) that accelerates the regeneration of bone or can be antibiotics in case of infection.

In another preferred embodiment the screws are bone implants that are not perforated and the filling is done through another opening or through the gap between the tube and the elevating screw. In this embodiment the tube is the filling conduit.

Figure 14:
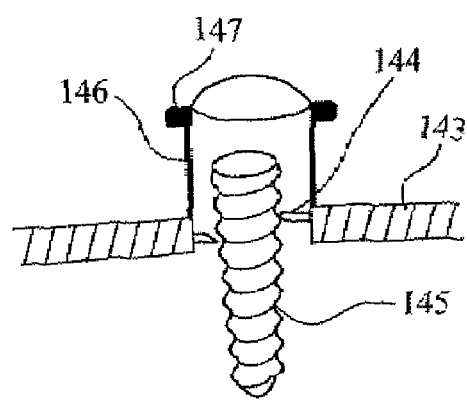
FIG. 14 is a sectional view illustrating the novel device for displacing the gums configured to be activated by pulling.

In another preferred embodiment illustrated in FIG. 14 the plate 143 is elevated by pulling instead of turning a nut as described above. The plate 143 has two projections 144, which are facing the elevating screw 145 preferably on the opposite side of the screw 145. One projection is higher than the second, in order to fit the spaces between the threads. The difference is approximately half the step of the thread of the elevating screw 145. The tube 146 includes also two projections 147 configured to allow a pooling tool to hold the tube 146 and push the elevating screw 145 resulting in elevating of the tube 146 and the plate 143 The projections 144 of the plate are configured to allow elevation of the plate and to resist forces trying to lower the plate. The tube 146 preferably is sealed and fixated as described in the previous embodiment. In this embodiment as in all the embodiments described above and later a gradual and controlled displacement of the soft tissue from the bone can be achieved.

In another preferred embodiment the plate is configured to allow replacement of the elevating screw with the final dental implant without taking the device out. In this embodiment the dental implant can be inserted in an early phase and shorten the treatment time. The elevating screw is preferably narrow in order not to interfere with the process of bone regeneration and to reduce the hole in the gums. The final dental implant is preferably wide in order to have more surface attached to the bone. Therefore it is recommended to replace the elevating screw, which can be also perforated and hollow with a final dental implant. The replacement can be done after the plate has reached its final location and the filling is complete. The tube in this embodiment is threaded to the plate and they are not one piece. The hole in the plate after removing the tube should be at least 3.8 mm to allow the insertion of a regular 3.75 mm dental implant. After the tube is removed from the plate the elevating screw is taken out through the hole in the plate and the final dental implant is inserted instead. After the final dental implant is inserted to the bone a cover screw is screwed inside the dental implant (in the preferred case of an implant with an internal thread) and engaged the threads in the hole of the plate. In this state, the dental implant stabilizes the plate. The cover screw has one region with threads that are compatible with the internal threads of the dental implant and a second region that the threads fits the threads of the hole in the plate and a region that seals the connection between the plate and the cover screw. In this configuration for every dental implant in the market a special cover screw can be developed. After the insertion of the dental implant and the cover screw the bone is regenerated around the dental implant because the dental implant is surrounded by bone callus and preferably also by bone augmenting material. The process of osseointegration of the implant occurs simultaneously with the regeneration of the bone therefore the treatment is shorter. It is also possible to place a final dental implant on top of at least part of the elevating screw therefore no need to take all the elevating screw out.

The foregoing procedure has been described in terms of the mandible. Of course, the same procedure can also be applied to reconstruction of the maxilla and other bones and for other tissues in the body.

Figure 15A:
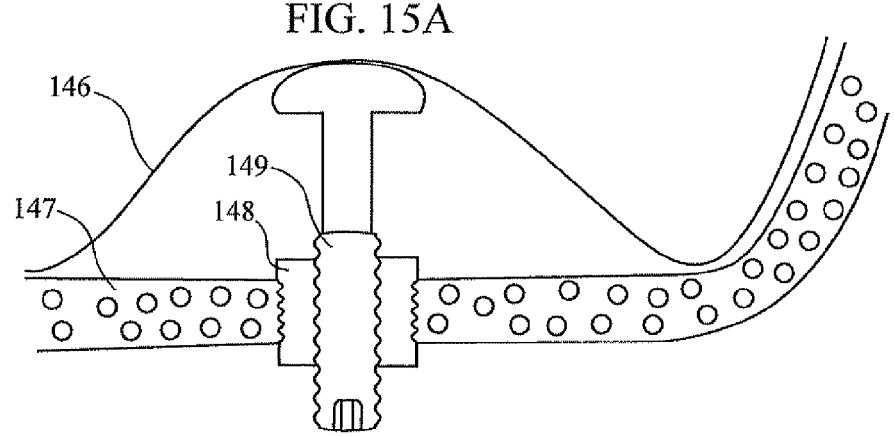
FIG. 15A is a sectional view illustrating a novel device for displacing the membrane of the maxillary sinus.

The method can be applied also for sinus lift. In a sinus lift procedure, which is a well-known procedure, the membrane lining the sinus, the Schneiderian membrane, is elevated and displaced from the bone of the floor of the sinus. The gap between the elevated membrane and the floor of the sinus is filled with bone augmenting material. The procedure is relatively difficult since the Schneiderian membrane is very delicate and can be easily torn when trying to disconnect the membrane from the bone. In the new method of this invention that can be called "Schneiderian distraction", the membrane is elevated gradually therefore the detachment of the membrane requires small forces and the chances of tearing the membrane are smaller. If the process takes several days the membrane can proliferate and enlarge and therefore can be elevated more easily. FIG. 15 illustrates a cross section of the maxillary sinus after the device for elevating the membrane 146 is inserted through a hole in the alveolar ridge 147. The device is made from two parts, the external part 148 is preferably a screw with threads on the outside and the inside aspects. The internal part 149 is a screw that its external threads match the internal threads of the external part. The upper part of the internal screw is preferably wide, rounded and smooth to minimize the chances of tearing the membrane 146. The internal screw 149 is threaded inside the external screw 148 so the upper segments of the internal one is at the same level as the upper segment of the external one. The device is inserted through the alveolar ridge 147 to reach the floor of the sinus in the same way that a regular dental implant is inserted beneath the maxillary sinus. After the insertion of the device it is recommended to wait for several days before activating the device. In this period the membrane can be healed and closed in case it was injured in the insertion of the device. After waiting for several days the internal screw 149 can be turned every day or every several days so it will push the membrane 146. It is recommended to elevate the screw 1-2 mm each time. After several elevations of the internal screw the membrane is several millimeters above the floor of the sinus as illustrated in FIG. 15A so bone can regenerate beneath the membrane. It is recommended to use several devices each one in the place where the future dental implant is to be placed. The use of several devices will simplify the elevation of the membrane. After the membrane is elevated it is recommended to wait for several months to allow the bone to grow. There is no need however to wait several months with the device in the sinus. It is recommended to take the device out just after the last elevation of the membrane or several days later and immediately to insert the final dental implant. In a preferred embodiment before inserting the final dental implant bone augmenting material is inserted through the hole in the alveolar ridge to fill the space between the membrane and the floor of the sinus. In these embodiments the bone will regenerate and the implant will be osseointegrated at the same time therefore reducing the treatment time.

Figure 15B:
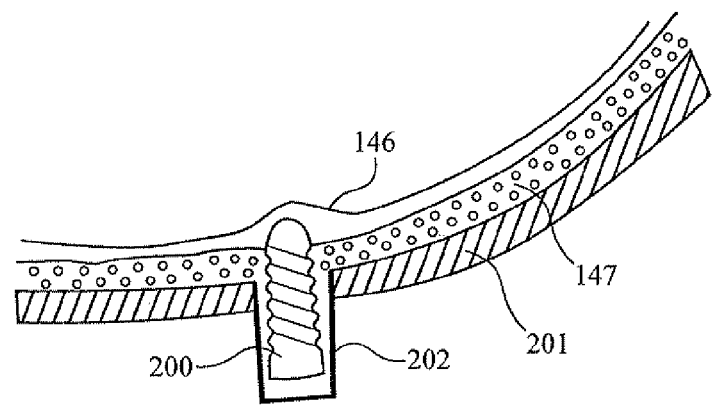
FIG. 15B is a sectional view illustrating another novel device for displacing the membrane of the maxillary sinus.
Figure 15C:
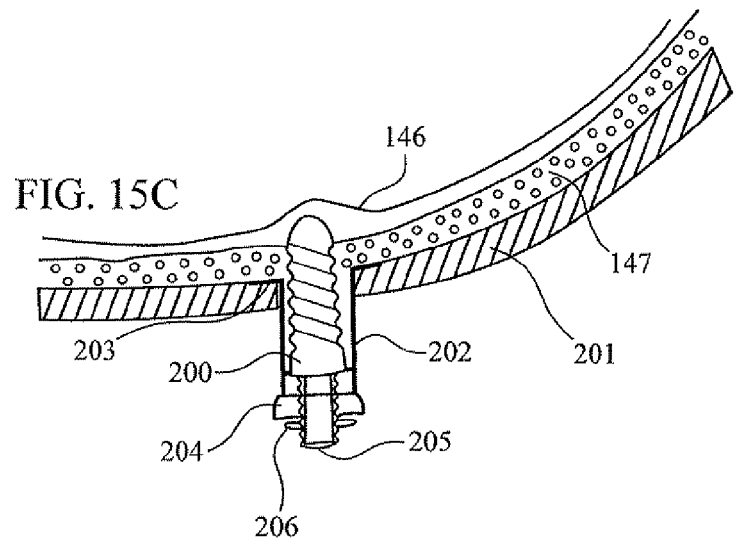
FIG. 15C is a sectional view illustrating a novel device for displacing the membrane of the maxillary sinus and the periosteal tissue.

In another preferred embodiment the elevating screw can be the final dental implant therefore eliminating the need to replace the device with the final dental implant. FIG. 15B is describing a preferred embodiment using the final dental implant as the elevating screw. The preferably tapered implant 200 with preferably round apical region and preferably threads along the body of the implant is inserted through the alveolar ridge to reach the Schneiderian membrane 146. The implant is protruding through the gums 201 to the oral cavity. Over the implant 200 a tube 202 is placed reaching the alveolar bone 147. The tube 202 preferably has a sealing means at its coronal region. The tube can be made of biocompatible metal like titanium and the sealing means can be a titanium screw screwed to the tube or to the implant or a silicon plug. The tube 202 preferably is tightly fitted to the coronal region of the implant 200 in order to stabilize the tube or to have threads matching the threads of the implant. The tube preferably can be made from a biocompatible polymer or biocompatible elastic material like silicon or Teflon. In this preferred embodiment the internal diameter of the silicon tube is slightly smaller than the diameter of the coronal region of the implant. In this embodiment the tube 202 is forced over the implant so the tube is stabilized by the implant that is fixated to the bone and the tube is sealing the surface of the implant from the oral cavity because it is tightly fitted to the coronal region of the implant. In this embodiment a plug can be used to seal the tube but it is not necessary. Preferably the most coronal region of the implant about 1 mm is straight and not tapered to allow good sealing with the silicon. The silicon has to be clean and sterile in order not to contaminate the surface of the implant. The tube can also include threads to match the implant. In a preferred embodiment the tube like cover of the implant is connected to the mount of the implant and not to implant itself avoiding the contact with the implant surface. The tube like cover of the implant can be rigid like titanium be can also be flexible and to allow easy cutting of the tube. The tube is preferably transparent so the dentist can see the exact location of the implant inside the tube. Several days after the insertion of the implant the implant is screw into the sinus in a rate of 0.5-2 mm a day or every several days. The implant 200 is elevating the Schneiderian membrane 146 and the gap between the Schneiderian membrane 146 and the bone 147 will be filled with new bone tissue. As the implant is inserted the silicon tube can be shortened. When the implant is completely inside the bone the tube can be taken out and a healing screw is screwed to the implant. The tube is preferably transparent so the dentist can see the exact location of the implant.

Figure 23A:
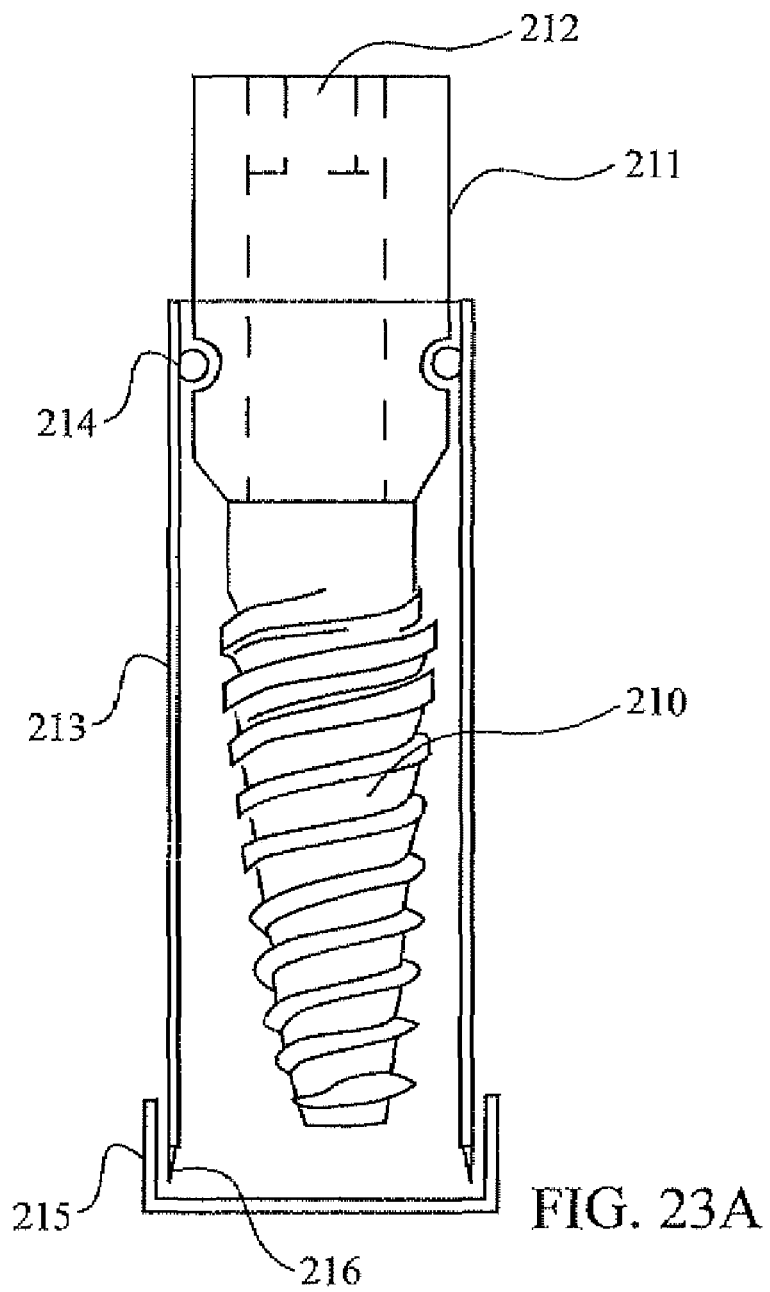
FIG. 23A is a sectional view demonstrating a protective cover to a dental implant to protect the implant in the time of the insertion.
Figure 23B:
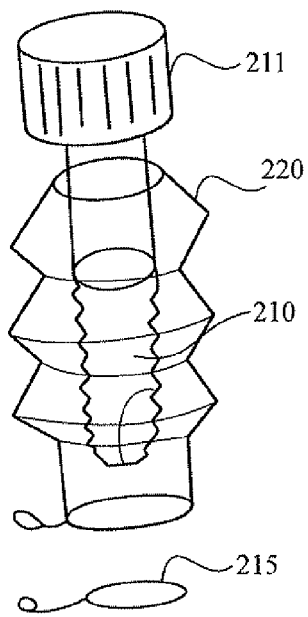
FIG. 23B is a sectional view demonstrating embodiment of a protective cover to a dental implant to protect the implant in the time of the insertion.
Figure 23C:
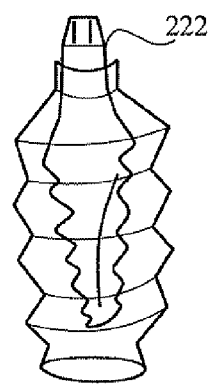
FIG. 23C is a sectional view demonstrating embodiment of a protective cover to a dental implant to protect the implant in the time of the insertion.
Figure 23D:
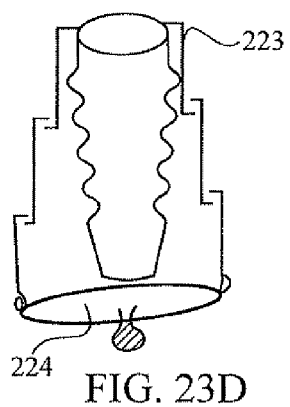
FIG. 23D is a sectional view demonstrating embodiment of a protective cover to a dental implant to protect the implant in the time of the insertion.
Figure 23E:
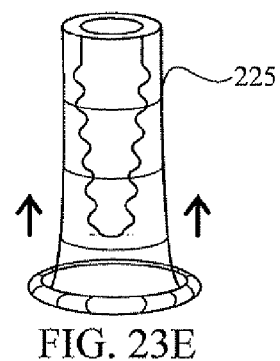
FIG. 23E is a sectional view demonstrating embodiment of a protective cover to a dental implant to protect the implant in the time of the insertion.

The tube can be placed over the implant after inserting the implant into the bone or the implant can be supplied with the tube on it. A dental implant inside a protecting cover like a silicon tube can be used regularly to protect the surface of the implant from air contamination like dust and saliva contamination while the implant is screwed inside the bone. This feature is not limited to distraction implants but can serve any dental implant to protect its surface. As the implant is inserted the protective sleeve is left above the bone and automatically released as the implant is completely inside the bone. FIG. 23 is demonstrating several embodiments of a protective cover to the implant that are connected to the implant while the implant is inserted. The preferred embodiments of FIG. 23 demonstrate covers that are not touching the implant surface and are getting automatically shorter as the implant is inserted inside the bone and the cover is left above the bone. The embodiments of FIG. 23 preferably are supplied with the cover allowing the dentist to take the implant from its package and to insert it without exposing the implant surface to the air, the saliva, the soft tissues and the instrument in the patient's mouth. FIG. 23A is demonstrating one embodiment of a dental implant 210 connected to a mount 211 which is slightly wider than the implant. The mount 211 at its upper region has a hole with an anti rotational mechanism 212 like an internal hex. (The mount 211 can be used also as a transfer copping). At least part of the mount and the implant are inside a tube-like cover 213. The internal diameter of the tube 213 is fitted to the external diameter of the mount 211 so the mount 211 can move inside the tube 213 with minimal force but when holding only the mount 211 the tube 213 is not falling because of friction. Preferably the mount 211 has a slot and a rubber like band inside the slot 214. The rubber is connecting the mount 211 to the tube 213 and allowing the mount to move inside the tube. The rubber band also is sealing the implant surface from contamination from above. Preferably the tube has a sealing plug 215 at its lower region. To insert the implant the dental surgeon holds the mount 211 and the tube 213 and take off the sealing plug 215. Then the dental surgeon is placing the implant over the bore in the bone he has already prepared and start to rotate the implant. The dental surgeon can use a hex tool that match the internal hex 212 inside the mount and a ratchet for the insertion of the implant. As the implant 210 is inserted the tube 213 is staying above the bone and the mount 211 is entered inside the tube. Because the diameter of the mount 211 is larger than the diameter of the implant 210 the implant 210 is not touching the tube 213 as the implant 210 is inserted. The tube 213 is preferably transparent to allow the dental surgeon to see the implant inside the tube in respect to the bone all the time of the insertion. The tube can be rigid or semi-rigid made from materials like PVC or other transparent plastic or polymers. The tube can be made from a biocompatible elastic materials like silicon so the tube 213 is slightly pressing the mount 211. The most lower region of the tube 216 can be made from a soft material like a thin layer of Teflon or silicon that will adapt better to any bone morphology therefore protecting more the surface of the implant. In another preferred embodiment the plug 216 is made from a soft biocompatible material like silicon and the dental surgeon is cutting the plug instead of taking it off. The plug is cut so to leave some excess of the soft walls of the plug below the tube that will function to adapt better to the bone and protect better the implant. The plug's walls preferably getting wider towards the bone to prevent the plug from bending towards the implant. After the implant is inside the bone the mount 211 is released from the implant 210 and the mount with the tube 213 are taken out. In FIG. 23A the tube is staying as it is on the bone in the rest embodiments of FIG. 23 the cover is getting shorter as the implant is inserted. FIG. 23B is demonstrating a foldable cover 220 that protect an implant 210 attached to a mount 211. The foldable cover 220 has also an apical plug 215 that the surgeon is pulling. As the implant is inserted the cover 220 is folding without touching the implant and become shorter. FIG. 23C is demonstrating a one piece implant with a foldable cover that is attached to the protruding prosthetic element 222 of the implant. FIG. 23D is demonstrating a cover in the shape of a telescope 223 having also a detachable plug 224 at its bottom. The telescope is getting shorter as the implant is inserted. The telescope can be made from titanium, deralin, silicon and any other approved biological packing material. FIG. 23E is demonstrating a rolling cover 225. As the implant is inserted the cover is rolling on itself upwards and is getting shorter. The cover can also include a spring assisting in the process of shortening the cover tube. The basic principle is to have the device that is going to be inserted inside the body inside a protective preferably transparent cover that will protect the device from air contamination until the device is inserted. In this novel concept there is no need to take the device out from its internal package but instead to push it through the cover that has an opening at the opposite side which is facing the body. This principle is not limited to dental implants but can reduce the incidence of infection in other fields of medicine: In orthopedics using bone implant, bone screws, bone plates, artificial joint etc that should be supplied in such a cover. In plastic surgery using tissue expanders, breast implants etc. In cardiac surgery using catheters the catheter should be inside a protective sleeve. Even when inserting a needle for infusion the needle is preferably protected. The tube to cover the dental implants as described above are especially useful since the procedure of placing dental implants are usually done in private clinics which don't have the sterile condition of a hospital and the procedure is done in a non sterile environment—the mouth.

In another preferred embodiment the Schneiderian distraction can be combined with the periosteal distraction. In many cases there is enlargement of the maxillary sinus and resorbtion of the alveolar bone so in order to place the dental implant in the correct vertical position the alveolar bone has to be augmented in both directions downwards towards the oral cavity and upwards towards the sinus. In this preferred embodiment illustrated in FIG. 15C the tube is connected to a subperiosteal plate 203 like the devices of FIG. 13-14. To the tube a cap 204 is threaded. The cap 204 has internal thread. To the implant a hollow screw 205 is attached and protruding through the cap 204 towards the oral cavity. The threads of the hollow screw 205 match the internal threads of the cap 204. The hollow screw 205 is attached to the implant 200 by an abutment screw (not shown) passing through the hollow screw into the internal threads of the implant like a regular abutment screw that attach an abutment to a dental implant. The hollow screw preferably has on its coronal region an internal hex or any other feature to allow the dentist to rotate the hollow screw. When the abutment screw is slightly released the hollow screw can be rotated resulting in the movement of the tube 202 and the plate 203 downwards and displacement of the gums 201 from the bone 147. Preferably the device includes a stabilizing element like a nut 206 threaded on the hollow screw 205 and fixating the cap 204 to the hollow screw 205, which is fixated to the dental implant 200 by the abutment screw. When the nut 206 is released and the abutment screw is not, rotating of the hollow screw 205 will rotate the implant 200 and will insert the implant 200 into the sinus, if the thread step of the hollow screw 205, match the thread step of the implant 200. In case the thread step of the hollow screw 205 is larger than the thread step of the implant 200 the plate 203 will be displaced also from the bone. The dentist can take out the hollow screw and rotate only the implant and then to screw again the hollow screw 205 and rotate it to displace the plate 203. Preferably there are several caps 204 with different heights that can be replaced as the implant 200 is inserted and the plate displaced. Preferably there is a plug to seal over the cap 204 and the hollow screw 205 to prevent bacteria to penetrate through the threads of the hollow screw. Preferably the connection of the cap 204 to the tube 202 is also sealed. The embodiment of FIG. 15C allows to place the implant at the correct position an to regenerate the bone at the apical region and the coronal region of the implant.

Theoretically the device can be a dental implant with a round smooth apical region and threads along the body of the implant and preferably a tapered implant. The implant is inserted through the alveolar ridge to reach the Schneiderian membrane so the coronal region of the implant is protruding through the gums to the oral cavity. After several days of healing the implant is gradually inserted about 1 mm a day and the Schnederian membrane is elevated Because the implant is tapered it is kept stable during the insertion. The problem with using only a dental implant is that the surface of the implant that is left open to the gums and to the oral cavity is contaminated. The contaminated surface has poor chances to develop osteointegration meaning good contact to the bone and even the potential of causing sinus infection. In the preferred embodiments of this invention the implanted element that starts outside the tissue and ends inside the tissue is protected from the oral cavity so when this surface is entered into the bone and to the sinus it can allow safe bone formation. This principle can be seen in all the embodiments of FIG. 1-15.

In a preferred embodiment the internal screw is hollow and perforated to allow insertion of bone augmenting material through the screw to the new space between the membrane and the floor of the sinus. The external screw includes also a sealing screw in order to prevent penetration of bacteria to the sinus and to prevent leakage of the bone augmenting material.

In another preferred embodiment the device includes a non rotating element above the internal screw. This non rotating element is elevated as the internal screw is elevated. The non rotating element has preferably a wide, round and smooth upper region and two thin projections in the lower region. The threads in the internal aspect of the external screw has two vertical slots that matches the projections of the non rotating element. The advantage of using a non-rotating element for pushing the membrane is that the rotation can tear the membrane. In another preferred embodiment the non-rotating element can be elevated by pushing and not by screwing of another internal screw. In this embodiment the internal aspect of the external screw will include small projections and the non-rotating element will include also projection to function in the same principle as illustrated in FIG. 4B and FIG. 14. In a preferred embodiment the non-rotating element is hollow and perforated. In another preferred embodiment the internal element can be elevated by screwing or by pushing. In this embodiment the internal element has two projections that project between the threads of the internal threads of the external part, preferably on the opposite side of the screw. One projection is higher than the second in order to fit the spaces between the threads. The difference is approximately half the step of the thread of the elevating screw. The tube includes also two projections configured to allow a pushing tool to hold the tube and push the internal element resulting in elevating of the internal element. The projections of the internal element are configured to allow elevation of the internal element and to resist forces trying to lower the internal element. The tube preferably is sealed as described in the previous embodiments. This device resembles the device of FIG. 14 but in this embodiment the tube is fixated to the bone and the internal screw is moving whereas in FIG. 14 the internal screw is fixated to the bone and the tube is moving. In this embodiment as in all the embodiments described above and later a gradual and controlled displacement of the soft tissue in this case the Schneiderian membrane from the bone can be achieved.

In the embodiments described above it is recommended to use several internal elements or elevating screws with different lengths in order to allow the use of a short external part or tube and to achieve large displacement of the soft tissue. In these embodiments the internal element or the elevating screws should be configured to be easily taken out and replaced with a longer internal element or elevating screw.

In another preferred embodiment the membrane is elevated by a balloon. In this embodiment a balloon, which is connected, to a cannula is inserted beneath the Schneiderian membrane. The balloon preferably made from silicon is then inflated every several days to elevate the membrane 1-2 mm each time. After the elevation, the device is taken out and the final dental implant is inserted. In a preferred embodiment before inserting the final dental implant bone augmenting material is inserted through the hole in the alveolar ridge to fill the space previously occupied by the balloon. The balloon is preferably designed to enlarge more horizontally than vertically therefore reducing the chances of tearing of the membrane.

Figure 16B:
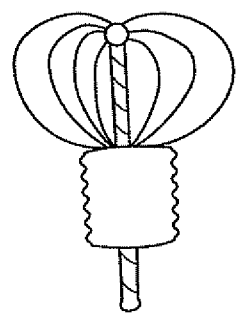
FIG. 16B is a perspective view of the device of FIG. 16A when activated to peel the membrane horizontally.
Figure 16A:
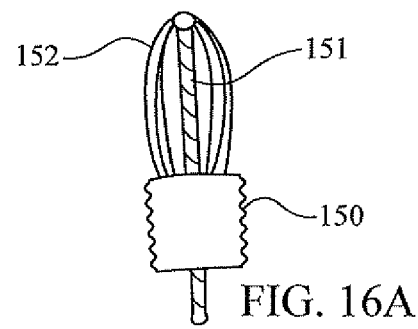
FIG. 16A is a perspective view illustrating the novel device for displacement of the membrane of the sinus configured to allow horizontal peeling of the membrane.
Figure 16C:
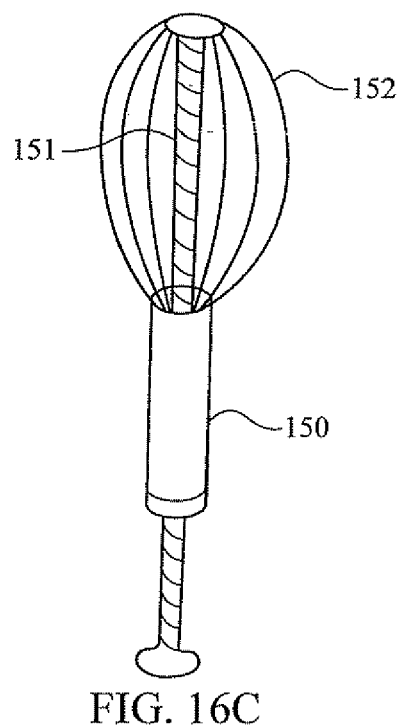
FIG. 16C is a perspective view of the novel device configured to widen a tunnel in the body.

In another preferred embodiment the device illustrated in FIGS. 16A, B and C includes an external tube 150 and internal rod 151. One edge of the external tube and one edge of the internal rod are connected by several flexible fibers 152 all around the edges of the external tube 150 and the internal rod 151. The connecting fibers 152 are configured to bend in the longitudinal dimension of the device without rotating around the longitudinal axis. When the internal rod 151 is pushed to protrude outside the internal tube the fibers form the geometry of a narrow tube as illustrated in FIG. 16A. When the internal rod 151 is moved to enter the external tube 152 the fibers form the geometry of a ball as illustrated in FIG. 16B. The device of FIG. 16A is for insertion beneath the Schneiderian membrane of the maxillary sinus. The device of FIG. 16C is for insertion between the bone and the gums. When the device is for subperiosteal insertion the insertion is preferably by using the tunnel technique, when the internal rod is outside the external tube. After the insertion of the device the internal rod is gradually pulled to enter the external tube. As the rod moves the fibers are expanding and pushing the gums and creating a space between the bone and the gums. The movement of the internal rod is preferably controlled by using a screw mechanism or using the mechanism of small projection as described above. In a preferred embodiment the external tube has internal threads and the internal rod is a screw. The internal screw is connected to a small plate in a connection configured to allow rotation of the screw without rotation of the plate but when the internal screw is moving in the longitudinal dimension the plate is moving with the screw. The plate is connected to the connecting fibers instead of the internal screw as described in the previous embodiment. In a preferred embodiment the internal screw is hollow and perforated to allow the insertion of bone augmenting materials to the space between the bone and the gums.

Figure 17:
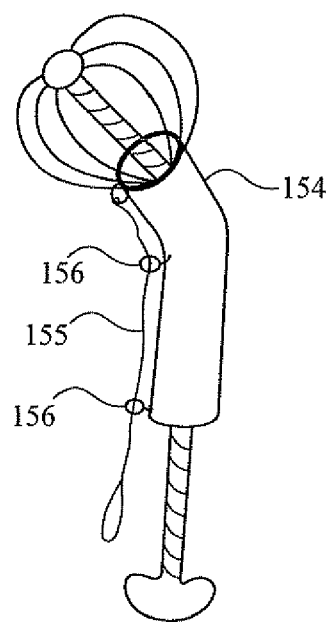
FIG. 17 is a perspective view illustrating the devices of FIGS. 16, 17 with the capability to control the bending of the device.
Figure 18:
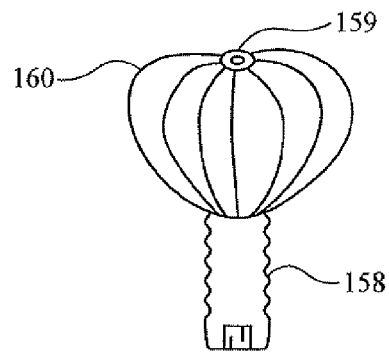
FIG. 18 is a perspective view illustrating the device for elevating the membrane of the sinus by elastic fibers forming a spherical morphology.
Figure 19:
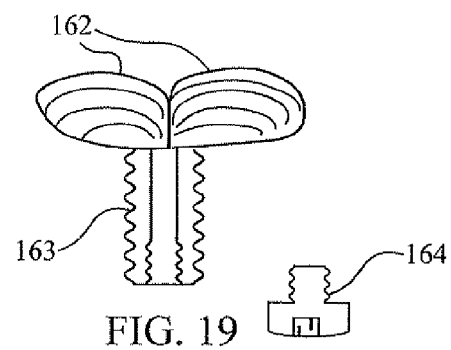
FIG. 19 is a perspective view illustrating the device like the device of FIG. 18 that has two spherical regions.
Figure 20:
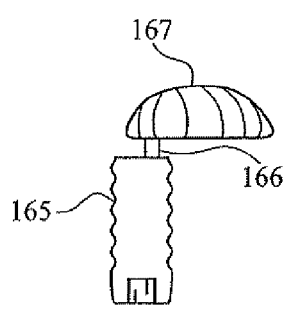
FIG. 20 is sectional view illustrating the device for peeling the membrane by using a hollow dental implant and eccentric internal element.
Figure 21:
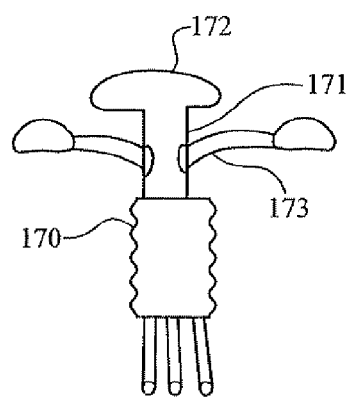
FIG. 21 is a perspective view illustrating the device for elevating the Schneiderian membrane by bendable fibers inside a central tube.

The device described above can be used not only for separation of the gums from the bone but also to create and enlarge tunnels in other regions of the body. This device can be used also for the displacement of the Schneiderian membrane. In a preferred embodiment for sinus lift the device of FIGS. 16A and B is inserted inside a tube, which is inserted through the alveolar ridge to reach the floor of the sinus. After the device is placed inside the tube it is gradually advanced upwards preferably 1-2 mm every day while the connecting fibers are in the shape of a narrow tube. After the upper edge of the external tube of the device reaches the floor of the sinus and the internal element protruding to the sinus and the desired vertical displacement of the membrane is achieved the internal element is advanced downwards resulting in horizontal expansion of the connecting fibers. This horizontal expansion will peel the membrane from the bone. This expansion is preferably done also gradually. After the maximal horizontal expansion was reached the device is gradually advanced upwards resulting in displacement of a larger area of the membrane. The advancement of the device inside the tube can be by screwing the device of FIG. 16A inside the tube if the tube has internal threads. In a preferred embodiment illustrated in FIG. 17 the external tube of the device is flexible and the bending of the device can be controlled. This control can be achieved by using a bendable external tube 154 and a wire 155. The wire 155 is configured to bend the tube when the wire is pulled for example by moving the wire through loops 156 placed along the tube 154. This configuration allows peeling the membrane from a larger area then the previous device illustrated in FIGS. 16A and B. In another embodiments illustrated in FIGS. 18,19 there are some examples of methods and devices to peel and displace the Schneiderian membrane vertically and horizontally through a small hole in the alveolar ridge beneath the maxillary sinus. These devices allow peeling the membrane from a larger diameter than the diameter of the hole in the alveolar ridge. In these methods and devices the devices are enlarged horizontally inside the sinus. The device of FIG. 18 includes a bone implant 158 connected to a small plate 159 by elastic bendable fibers 160. The relaxed state of the fibers 160 is when they are bended and creating a spherical morphology. The device is inserted through a narrow hole in the alveolar ridge to enter the maxillary sinus by unbending the fibers to form a narrow cylindrical morphology. After the fibers enter to the sinus they expand horizontally and peels the Schneiderian membrane from the floor of the sinus. In another preferred embodiment illustrated in FIG. 19 the device can be made from two spherical elements 162. This configuration allows getting more horizontal expansion. The dental implant 163 is preferably hollow to allow insertion of bone augmenting materials inside the sinus. If the dental implant is hollow it preferably should include a sealing element 164 to prevent infection to enter the sinus through the dental implant. In another preferred embodiment illustrated in FIG. 20 the device includes a hollow bone implant 165 and inside there is an internal rod 166 connected to a wider eccentric region 167 which projects horizontally at one side out of the implant. By rotating the internal element 166 the eccentric region 167 is displacing the membrane. This dental implant should also to be sealed. In another preferred embodiment illustrated in FIG. 21 the dental implant 170 is hollow and inside the dental implant there is a tube 171. The upper region 172 of the tube is preferably wider rounded and smooth so by pushing the tube upwards it is displacing the membrane of the sinus vertically. The tube has inside one or two longer elastic fibers 173 that are getting out of the tube through openings at the side of the tube and project horizontally. The amount of the horizontal projection can be controlled by moving the fibers 173 up and down. The fibers 173 are also projecting out side the tube downwards to allow access to the fibers. This device allows therefore vertical and horizontal displacement of the membrane. The tube can be rotated to allow the fibers to reach all the area of the sinus. The end of the fibers 174 is preferably rounded and smooth. The method of using a balloon as described above is using a similar principle.

Figure 22A:
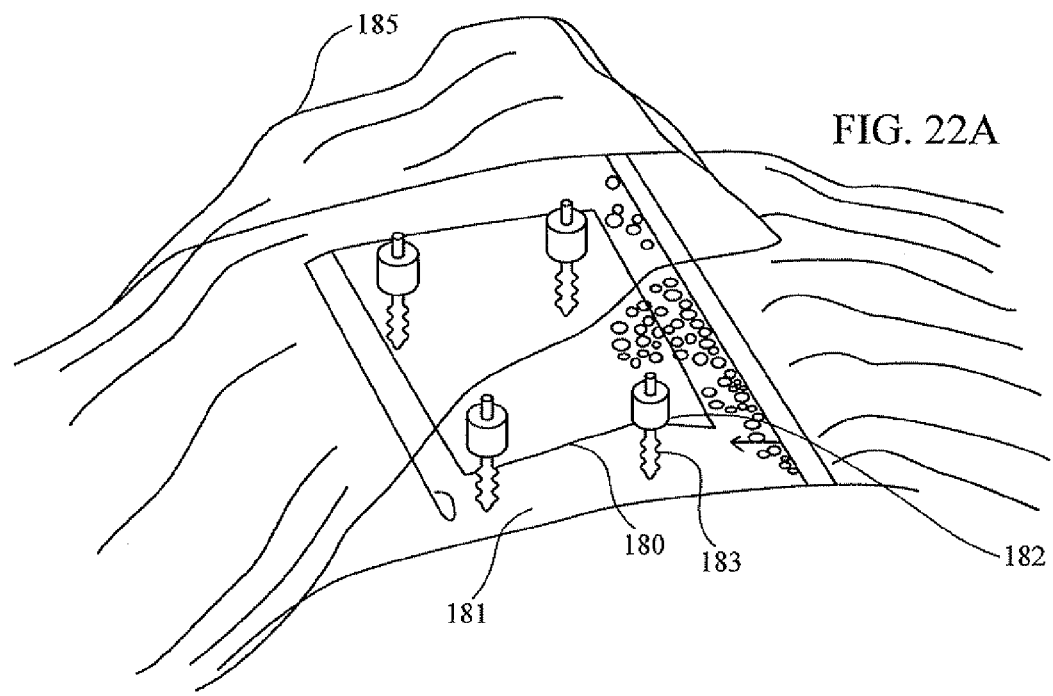
FIG. 22A is a perspective view of the novel device for displacing the gums and to promote the soft tissue regeneration
Figure 22B:
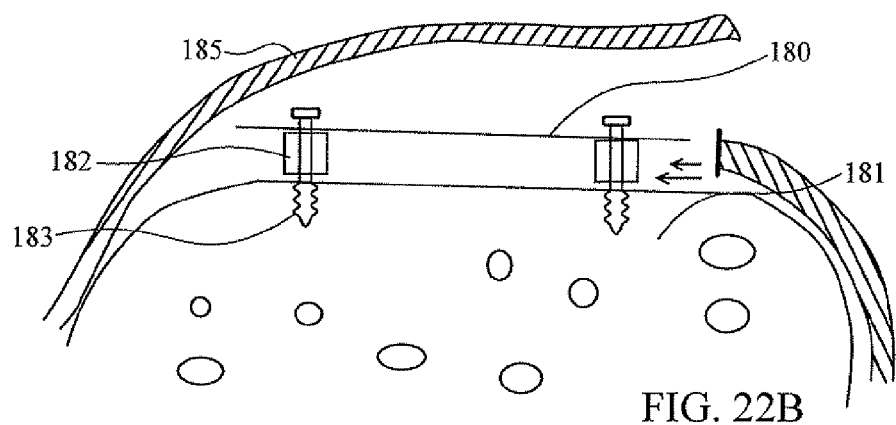
FIG. 22B is a sectional view of the novel device of FIG. 22A.

The above embodiments are trying to regenerate bone between the bone and the soft tissue. Bone regeneration can be achieved only if some conditions exist: 1) The space between the bone and the soft tissue is closed and bacteria cannot penetrate. 2) The movable element is stable. 3) The displacement is slow enough (about 1 mm per day) 4) The movable element is made from materials that don't interfere with bone regeneration. 5) There is no epithelial tissue that can penetrate the space. If one of these conditions doesn't exist instead of bone the soft tissue will regenerate. In most cases this is not the desired outcome. In some clinical cases achieving more soft tissue can be important. It can be important for aesthetic reasons and for cases when a large bone augmentation is needed. In these cases an excess of soft tissue can allow to achieve a good closure of a region where bone was implanted. The regeneration of the soft tissue takes several days so in case that jaw reconstruction is needed several days before the operation the periosteal tissue is elevated and the device of FIGS. 22A and B is implanted. The device includes a barrier 180 configured to be placed above the bone 181. The barrier 180 is placed above some elevating elements so as to create a space between the bone 181 and the barrier 180. The elevating elements can be small screws 183 inserted inside the bone 181. The elevating elements are configured to control the distance between the barrier 180 and the gums 185. This control can be achieved by using small nuts 182 threaded on the small screws 183. In another preferred embodiment the barrier can include some projections facing the bone. Preferably the barrier is allowed to have minor movements. Preferably the barrier is made from materials that don't allow bone regeneration like a bandage or a gauze or silicon but it can be done also with titanium. After the insertion of the barrier the gums 185 are sutured above the barrier preferably leaving at least one region open to the oral cavity. After several days the epithelial tissue will proliferate beneath the barrier 180 as illustrated by the arrows in FIGS. 22A and B and the result will be double layer gums. One layer beneath the barrier touching the bone, which is a new tissue and the second layer above the barrier, which are the original gums. The double layer gums can be used to cover large areas of the treated jaw. The barrier 180 and the elevating elements 182,183 are taken out. Preferably the barrier doesn't allow proliferation of tissue through the barrier in order to allow taking the barrier out easily.

Although the present invention has been described and illustrated in the context of certain preferred embodiments, it will be understood that modifications may be made without departing from the spirit of the invention.

What is claimed is:

1. A method for expanding, stretching, displacing or regenerating tissues comprising:
   (a) inserting at the bone soft tissue interface at least part of a displacing device, said displacing device includes a soft tissue displacer and a displacing element configured to displace said soft tissue displacer from the surface of said bone so as to displace said soft tissue to create a space between said bone and said soft tissue, said device is configured to allow new tissue ingrowth into said space while said soft tissue displacer is between said bone and said soft tissue, said soft tissue displacer includes a protruding element rigidly connected to said soft tissue displacer configured to protrude through said soft tissue;
   (b) displacing said soft tissue displacer from the surface of said bone so as to displace said soft tissue.

2. The method of claim 1, wherein said bone is the alveolar ridge and said bone is left open to the oral cavity.

3. The method of claim 1, wherein said soft tissue displacer is a movable element and said device is configured after activation to move said movable element said movable element is configured after said activation to induce forces displacing at least part of said soft tissue, said method includes activating of said device after insertion of said movable element between said soft tissue and said bone.

4. The method of claim 3, wherein said activation is performed in a plurality of stages separated by at least a number of hours, each stage incrementally displacing said soft tissue.

5. The method of claim 3, wherein the speed of said displacing of said soft tissue is appropriate for formation of bone callus between said bone and said soft tissue.

6. The method of claim 3, wherein said displacing is combined with introducing a bioactive filling material beneath said movable element.

7. The method of claim 3, wherein said protruding element is a filling conduit partially inserted into the tissue.

8. The method of claim 3, wherein said soft tissue is the periosteal tissue.

9. The method of claim 8, further comprising, prior to inserting said part of said displacing device, forming a subperiosteal tunnel for insertion of said part of said displacing device.

10. The method of claim 3, wherein said soft tissue is the Schneiderian membrane of the maxillary sinus or the nose.

11. The method of claim 3, wherein said displacing element is rigidly connected to said movable element.

12. The method of claim 3, wherein said activating is done at least partially by turning a screw.

13. The method of claim 3, wherein said device comprising a distorted elastic element trying to return to its original state.

14. The method of claim 3, wherein said movable element is configured so as to allow passage of materials from said soft tissue.

15. The method of claim 3, wherein said device comprising a reference element and said activation is done by inducing forces between said reference element and said movable element.

16. The method of claim 15, wherein said reference element is fixated to the bone.

17. The method of claim 16, wherein said reference element is a bone implant.

18. The method of claim 17, wherein said protruding element is a tube, so said bone implant is at least partially inside said tube.

19. The method of claim 10, wherein said device includes a mechanism to expand horizontally to reach horizontal diameter larger than the diameter of the hole said device was inserted through.

20. The method of claim 3, wherein said soft tissue displacer includes a rigid plate, the plane of said plate substantially parallel the surface of said bone, the height of said device inside the body between said bone and said soft tissue is enlarged as said displacing mechanism is activated.

21. The method of claim 3, wherein said device is configured not to separate said new tissue from said bone.

22. The method of claim 3, wherein said movable element includes a semi-rigid part.

23. A method for expanding, stretching, displacing or regenerating tissues comprising:
   (a) inserting at the bone soft tissue interface at least part of a displacing device comprising a soft tissue displacer, said device is configured after activation to displace said soft tissue displacer from the surface of said bone so as to displace said soft tissue to create a space between said bone and said soft tissue, said device is configured to allow new tissue ingrowth into said space while said soft tissue displacer is between said bone and said soft tissue, without separating said new tissue from said bone, said soft tissue displacer includes a protruding element rigidly connected to said soft tissue displacer configured to protrude through said soft tissue, the height of said device inside the body between said bone and said soft tissue is enlarged as said device is activated
   (b) displacing said soft tissue displacer from the surface of said bone so as to displace said soft tissue.

24. The method of claim 23, wherein said activation is performed in a plurality of stages separated by at least a number of hours, each stage incrementally displacing said soft tissue.

25. The method of claim 23, wherein said displacing is done continuously over a period of time.

26. The method of claim 23, wherein said displacing device includes a filling conduit partially inserted into the tissue.

27. The method of claim 23, wherein said displacing device is formed at least in part from a bio-dissipative material.

28. The method of claim 23, wherein said soft tissue is the periosteal tissue.

29. The method of claim 23, wherein said soft tissue is the Schneiderian membrane of the sinus or the nose.

30. The method of claim 29, wherein said device includes a mechanism to expand horizontally to reach horizontal diameter larger than the diameter of the hole said device was inserted though.

31. The method of claim 23, wherein said displacing device is configured to take a specific shape as said device is activated.

32. The method of claim 23, wherein said activation of said displacing device is done at least partially by turning a screw.

33. The method of claim 23, wherein said device comprising a reference element and said activation is done by inducing forces between said reference element and said soft tissue displacer.

34. The method of claim 33, wherein said reference element is fixated to the bone.

35. The method of claim 34, wherein said reference element is a bone implant.

36. The method of claim 35, wherein said soft tissue displacer includes a tube, so said bone implant is at least partially inside said tube.

37. The method of claim 34, wherein said reference element includes a tube, so said soft tissue displacer is at least partially inside said tube.

38. The method of claim 23, wherein said soft tissue displacer includes a rigid plate, the plane of said plate substantially parallel the surface of said bone.

39. The method of claim 23, wherein said movable element includes a protruding element configured to protrude outside the body.

40. A device for expanding, stretching, displacing or regenerating tissues comprising:
a soft tissue displacer for insertion at least partially to the bone soft tissue interface and a displacing element configured to displace upwards said soft tissue displacer in a vertical direction from the surface of said bone so as to displace said soft tissue to create a space between said bone and said soft tissue, said device is configured to allow new tissue ingrowth into said space while said soft tissue displacer is between said bone and said soft tissue, said soft tissue displacer includes a protruding element rigidly connected to said soft tissue displacer configured to protrude through said soft tissue, said soft tissue displacer includes a rigid plate to be located between said bone and said soft tissue, the plane of at least part of said plate being substantially perpendicular to said direction, at least one extension is extending from said part of said plate downwards and horizontally.

41. The device of claim 40, wherein said soft tissue displacer is a movable element and said device is configured after activation to move said movable element so as to induce forces displacing at least part of said soft tissue.

42. The device of claim 41, wherein said device is configured to allow said activation to be performed in a plurality of stages separated by at least a number of hours, each stage incrementally displacing said soft movable element.

43. The device of claim 41, wherein said device is configured to allow continuous displacing of said movable element.

44. The device of claim 41, wherein said device includes a filling conduit configured for insertion of materials beneath said movable element; said filling conduit configured so as to be accessible from outside the body.

45. The device of claim 41, wherein said activation is done at least partially by turning a screw.

46. The device of claim 41, wherein said device includes a reference element and said activation is done by inducing forces between said reference element and said movable element.

47. The device of claim 46, wherein said reference element is configured so as to be fixated to the bone.

48. The device of claim 47, wherein said reference element is a bone implant and said protruding element is a tube, so said bone implant is at least partially inside said tube.

49. The device of claim 47, wherein said reference element is a bone implant.

50. The device of claim 41, wherein the height of said device inside the body between said bone and said soft tissue is enlarged as said device is activated.

51. The device of claim 41, wherein said device is configured not to separate said new tissue from said bone.

52. The device of claim 41, wherein said device is configured to take a specific shape as said device is activated.

53. The device of claim 41, wherein said movable element is configured so as to allow passage of materials from said soft tissue.

54. The device of claim 41, wherein said movable element is a dental implant.

55. The device of claim 41, wherein said device comprising a distorted elastic element trying to return to its original state.

56. The device of claim 41, wherein said device includes a mechanism to expand horizontally to reach horizontal diameter larger than the diameter of the hole said device was inserted through.

57. The device of claim 41, wherein said movable element includes a semi-rigid part.

58. A device for expanding, stretching, displacing or regenerating tissues comprising:
a soft tissue displacer for insertion at least partially to the bone soft tissue interface, said device is configured after activation to displace upwards said soft tissue displacer in a vertical direction from the surface of said bone so as to displace said soft tissue to create a space between said bone and said soft tissue, said device is configured to allow new tissue ingrowth into said space while said soft tissue displacer is between said bone and said soft tissue, without separating said new tissue from said bone, said soft tissue displacer includes a protruding element rigidly connected to said soft tissue displacer configured to protrude through said soft tissue, said soft tissue displacer includes a rigid plate to be located between said bone and said soft tissue, the plane of at least part of said plate being substantially perpendicular to said direction, at least one extension is extending from said part of said plate downwards and horizontally, the height of said device inside the body between said bone and said soft tissue is enlarged as said device is activated.

59. The device of claim 58, wherein said device is configured to allow said activation to be performed in a plurality of stages separated by at least a number of hours, each stage incrementally displacing said soft tissue displacer.

60. The device of claim 58, wherein said device includes a filling conduit configured for insertion of materials beneath said soft tissue displacer; said filling conduit configured so as to be accessible from outside the body.

61. The device of claim 58, wherein said activation is done at least partially by turning a screw.

62. The device of claim 61, wherein said screw is hollow and perforated.

63. The device of claim 58, wherein said device includes a reference element and said device is configured so as to induces forces between said reference element and said soft tissue displacer.

64. The device of claim 63, wherein said reference element is configured so as to be fixated to the bone.

65. The device of claim 64, wherein said reference element is a bone implant and soft tissue displacer includes a tube protruding outside the body, so said bone implant is at least partially inside said tube.

66. The device of claim 64, wherein said reference element is a bone implant.

67. The device of claim 64, wherein said reference element includes a tube, so said soft tissue displacer is at least partially inside said tube.

68. The device of claim 58, wherein said plate is at least partially perforated.

69. The device of claim 58, wherein said device is configured to take a specific shape as said device is activated.

70. The device of claim 58, wherein said soft tissue displace is configured so as to allow passage of materials from said soft tissue.

71. The device of claim 58, wherein said soft tissue displacer is a dental implant.

72. The device of claim 58, wherein at least part of said device is configured so as to be pulled out easily from said tissue.

73. The device of claim 58, wherein said device includes a mechanism to expand horizontally to reach horizontal diameter larger than the diameter of the hole said device was inserted through.

* * * * *